(12) United States Patent
Roth et al.

(10) Patent No.: US 7,776,547 B2
(45) Date of Patent: Aug. 17, 2010

(54) CELLULAR ANALYSIS USING RAMAN SURFACE SCANNING

(75) Inventors: Mark Roth, Seattle, WA (US); Andrew Berlin, San Jose, CA (US); Selena Chan, Sunnyvale, CA (US); Tae-Woong Koo, Cupertino, CA (US); Xing Su, Cupertino, CA (US); Lei Sun, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 282 days.

(21) Appl. No.: 11/027,470

(22) Filed: Dec. 30, 2004

(65) Prior Publication Data

US 2006/0046313 A1    Mar. 2, 2006

Related U.S. Application Data

(63) Continuation-in-part of application No. 10/927,996, filed on Aug. 26, 2004.

(51) Int. Cl.
G01N 33/53 (2006.01)
(52) U.S. Cl. ............... 435/7.1; 436/524; 436/8
(58) Field of Classification Search ........... 436/512, 436/164, 174; 435/7.1, 7.2
See application file for complete search history.

(56) References Cited

U.S. PATENT DOCUMENTS

| | | | |
|---|---|---|---|
| 4,444,879 A | 4/1984 | Foster et al. | |
| 5,270,163 A | 12/1993 | Gold et al. | |
| 5,306,403 A | 4/1994 | Vo-Dinh | |
| 5,521,289 A | 5/1996 | Hainfeld et al. | |
| 5,567,588 A | 10/1996 | Gold et al. | |
| 5,670,637 A | 9/1997 | Gold et al. | |
| 5,696,249 A | 12/1997 | Gold et al. | |
| 5,712,105 A | 1/1998 | Yanaihara et al. | |
| 5,721,102 A * | 2/1998 | Vo-Dinh | 435/6 |
| 5,728,590 A | 3/1998 | Powell | |

(Continued)

FOREIGN PATENT DOCUMENTS

EP    0 587 008 A1    3/1994

(Continued)

OTHER PUBLICATIONS

Wilke et al. (Langmuir et al. 1991 vol. 7, p. 714-721).*

(Continued)

*Primary Examiner*—Jacob Cheu
(74) *Attorney, Agent, or Firm*—Pillsbury Winthrop Shaw Pittman LLP

(57) ABSTRACT

Methods and apparatus are provided for assaying cell samples, which may be living cells, using probes labeled with composite organic-inorganic nanoparticles (COINs) and microspheres with COINs embedded within a polymer matrix to which the probe moiety is attached. COINs intrinsically produce SERS signals upon laser irradiation, making COIN-labeled probes particularly suitable in a variety of methods for assaying cells, including biological molecules that may be contained on or within cells, most of which are not inherently Raman-active. The invention provides variations of the sandwich immunoassay employing both specific and degenerate binding, methods for reverse phase assay of tissue samples and cell microstructures, in solution displacement and competition assays, and the like. Systems and chips useful for practicing the invention assays are also provided.

33 Claims, 14 Drawing Sheets

U.S. PATENT DOCUMENTS

| | | | |
|---|---|---|---|
| 5,766,963 | A | 6/1998 | Baldwin et al. |
| 5,843,653 | A | 12/1998 | Gold et al. |
| 6,002,471 | A | 12/1999 | Quake |
| 6,174,677 | B1 | 1/2001 | Vo-Dinh |
| 6,180,415 | B1 | 1/2001 | Schultz et al. |
| 6,219,137 | B1 | 4/2001 | Vo-Dinh |
| 6,263,286 | B1 | 7/2001 | Gilmanshin et al. |
| 6,514,767 | B1 | 2/2003 | Natan |
| 6,537,498 | B1 | 3/2003 | Lewis et al. |
| 6,608,716 | B1 | 8/2003 | Armstrong et al. |
| 6,861,263 | B2 * | 3/2005 | Natan .................... 436/164 |
| 2002/0090662 | A1 * | 7/2002 | Ralph .................... 435/7.92 |
| 2002/0177143 | A1 * | 11/2002 | Mirkin et al. ............. 435/6 |
| 2003/0211488 | A1 | 11/2003 | Mirkin et al. |
| 2003/0232388 | A1 | 12/2003 | Kreimer et al. |
| 2005/0064435 | A1 | 3/2005 | Su et al. |
| 2005/0064604 | A1 | 3/2005 | Bohmann et al. |
| 2005/0089901 | A1 | 4/2005 | Porter et al. |
| 2005/0123974 | A1 | 6/2005 | Gilmanshin et al. |
| 2005/0130163 | A1 | 6/2005 | Smith et al. |
| 2005/0142567 | A1 | 6/2005 | Su et al. |
| 2005/0147963 | A1 * | 7/2005 | Su et al. .................... 435/5 |
| 2005/0147976 | A1 | 7/2005 | Su |
| 2005/0147977 | A1 | 7/2005 | Koo et al. |
| 2005/0186576 | A1 | 8/2005 | Chan et al. |
| 2005/0191665 | A1 | 9/2005 | Su et al. |
| 2006/0033910 | A1 | 2/2006 | Sun et al. |
| 2006/0046311 | A1 | 3/2006 | Sun et al. |
| 2006/0073336 | A1 | 4/2006 | Zhang et al. |
| 2006/0147941 | A1 | 7/2006 | Su |

FOREIGN PATENT DOCUMENTS

| | | |
|---|---|---|
| WO | WO 01/25758 A1 | 4/2001 |
| WO | WO 02/40698 A2 | 5/2002 |
| WO | WO 2005/062741 A2 | 7/2005 |
| WO | WO 2005/066370 A2 | 7/2005 |
| WO | WO 2005/066612 A2 | 7/2005 |
| WO | WO 2005/090948 A1 | 9/2005 |

OTHER PUBLICATIONS

Paweletz et al. (Oncognee 2001 vol. 20, p. 1981-1989).*
PCT International Search Report (dated May 10, 2007), International Application No. PCT/US2005/031582—International Filing Date Sep. 2, 2005, (19 pages).
Non-Final OA (mailed Apr. 9, 2007), U.S. Appl. No. 11/325,833, Filing Date Dec. 30, 2005, (16 pages).
Lei Sun, et al., "Composite Organic-Inorganic Nanoparticles as Raman Labels for Tissue Analysis", Nano Letters, 2007, vol. 7, No. 2 (pp. 351-356).
U.S. Appl. No. 11/527,895, Filed—Sep. 26, 2006, entitled Composite Organic Inorganic Nanoclusters as Carriers and Identifiers of Tester Molecules, Inventor—Xing Su.
Bruchez, "Qdot™ 655 Streptavidin Detection In Flow Cytometry," Quantum Dot Vision, Jun. 2003 (pp. 12-13).
Jain, "Nanotechnology in Clinical Laboratory Diagnostics", Clinica Chimica Acta, Amsterdam, NL, vol. 358, No. 1-2, Aug. 2005 (pp. 37-54), XP004976368, ISSN: 0009-8981.
Moore, et al., "Detection and Identification of Mycobacterium tubeculosis Directly from Sputum Sediments by Ligase Chain Reaction," Journal of Clinical Microbiology, vol. 36, No. 4, Apr. 1998 (pp. 1028-1031).
Nam, et al., "Nanoparticle-Based Bio-Bar Codes for the Ultrasensitive Detection of Proteins," Science Magazine, vol. 301, Sep. 26, 2003 (pp. 1884-1886).
PCT International Search Report—dated Nov. 9, 2005, International Application No. PCT/US2004/043878—International Filing Date Dec. 28, 2004 (P18027X2PCT) (16 pages).
Salata, OV, "Applications of Nanoparticles in Biology and Medicine," Journal of Nanobiotechnology, vol. 2, No. 3, Apr. 30, 2004 (6 pages).

"Strem Nanomaterials for Medical & Pharma Applications," Strem Chemicals Brochure, 2005 (2 pages).
Su, et al., "Composite Organic—Inorganic Nanoparticles (COINs) with Chemically Encoded Optical Signatures", Nano Letters, Jan. 2005, vol. 5, No. 1 (pp. 49-54), XP002350668, ISSN: 1530-6984.
U.S. Appl. No. 11/081,772, filed Mar. 15, 2005, entitled "Composite Organic Inorganic Nanoclusters", Inventors: Lei Sun, et al.
U.S. Appl. No. 11/216,112, filed Sep. 1, 2005, entitled "Multiplex Data Collection and Analysis in Bioanalyte Detection", Inventors: Xing Su, et al.
U.S. Appl. No. 11/325,833, filed Dec. 30, 2005, entitled "Degenerate Binding Detection and Protein Identification Using Raman Spectroscopy Nanoparticle Labels", Inventors: Yamakawa, et al.
Wu, et al., "Immunofluorescent labeling of cancer marker Her2 and other cellular targets with semiconductor quantum dots," Nature Biotechnology, Nature Publishing Group, vol. 21, Jan. 2003 (pp. 41-46).
Xu, et al., "Multiplexed SNP genotyping using the Qbead™ system: a quantum dot-encoded microsphere-based assay," Nucleic Acids Research, vol. 31, No. 8 e43, 2003 (10 pages).
Alivisatos, A. P., "Perspectives on the Physical Chemistry of Semiconductor Nanocrystals" *J. Phys. Chem.* 100, 13226-13239 (1996).
Bosnick, K. A., Jiang, J. & Brus, L. E. "Fluctuations and Local Symmetry in Single-Molecule Rhodamine 6G Raman Scattering on Silver Nanocrystal Aggregates" *J. Phys. Chem. B*. 106, 8096-8099 (2002).
Brody and Gold, "Aptamers as Therapeutic and Diagnostic Agents" *Reviews in Molecular Biotechnology*, 74:5-13 (2000).
Campion and Kambhampati, "Surface-Enhanced Raman Scattering" *Chem. Soc. Rev.* 27:241-250 (1998).
Cao et al., "Nanoparticles with Raman Spectroscopic Fingerprints for DNA and RNA Detection" *Science* 297:1536-1540 (2002).
Craighead, "Nanoelectromechanical Systems," *Science*, 290:1532-1535, 2000.
de Bruin et al., "Selection of High-Affinity Phage Antibodies from Phage Display Libraries" *Nat Biotechnol.* 1999; 17:397-399.
Doering and Nie, "Spectroscopic Tags Using Dye-Embedded Nanoparticles and Surface-Enhanced Raman Scattering" *Anal Chem.* 75:6171-6176 (2003).
Duffy, D., McDonald, J., Schueller, O. & Whitesides, G. Rapid Prototyping of Microfluidic Systems in Poly(dimethylsiloxane). *Anal. Chem.* 70, 4974-4984 (1998).
Emory et al., "Direct Observation of Size-Dependent Optical Enhancement in Single Metal Nanoparticles" *J. Am. Chem. Soc.* 120:8009-8010 (1998).
Fodor et al., "Multiplexed Biochemical Assays with Biological Chips" *Nature* 364:555-556 (1993).
Graham et al., "Simple Multiplex Genotyping by Surface-Enhanced Resonance Raman Scattering" *Anal. Chem.* 74:1069-1074 (2002).
Grubisha et al., "Femtomolar Detection of Prostate Specific Antigen: an Immunoassay Based on Surface-Enhanced Raman Scattering and Immunogold Labels" *Anal. Chem.* 75:5936-5943 (2003).
Isola et al., "Surface-Enhanced Raman Gene Probe for HIV Detection" *Anal. Chem.* 70:1352-1356 (1998).
Jaiswal et al., "Long-Term Multiple Color Imaging of Live Cells Using Quantum Dot Bioconjugates" *Nature Biotechnology* 12:47-51 (2003).
Jiang et al., "Single Molecule Raman Spectroscopy at the Junctions of Large Ag Nanocrystals" *J. Phys. Chem. B* 107:9964-9972 (2003).
Kambhampati et al., "On the Chemical Mechanism of Surface Enhanced Raman Scattering: Experiment and Theory" *J. Chem. Phys.* 108:5013-5026 (1998).
Kerker, M., "Electromagnetic Model for Surface-Enhanced Raman Scattering (SERS) on Metal Colloids" *Acc. Chem. Res.* 17:271-277 (1984).
Kneipp et al., "Ultrasensitive Chemical Analysis by Raman Spectroscopy" *Chemical Reviews* 99:2957-2975 (1999).
Kneipp et al., "Single Molecule Detection Using Surface-Enhanced Raman Scattering (SERS)" *Physical Review Letters* 78:1667-1670 (1997).
Kneipp et al. "Surface-Enhanced Raman Spectroscopy in Single Living Cells Using Gold Nanoparticles" *Appl. Spectroscopy* 56:150-154 (2002).

MacBeath and Schreiber, "Printing Proteins as Microarrays for High-Throughput Function Determination" *Science* 289:1760-1763 (2000).

Michaels et al., "Ag Nanocrystal Junctions as the Site for Surface-Enhanced Raman Scattering of Single Rhodamine 6G Molecules" *J. Phys Chem B* 104:11965-11971 (2000).

Michaels et al., "Surface Enhanced Raman Spectroscopy of Individual Rhodamine 6G Molecules on Large Ag Nanocrystals" *J. Am Chem Soc.* 121:9932-9939. (1999).

Mulvaney et al., "Glass-Coated, Analyte-Tagged Nanoparticles: A New Tagging System Based on Detection with Surface-Enhanced Raman Scattering" *Langmuir* 19:4784-4790 (2003).

Ni, et al., "Immunoassay Readout Method Using Extrinsic Raman Labels Adsorbed on Immunogold Colloids" *Anal. Chem.* 71:4903-4908 (1999).

Nicewarner-Pena et al., "Submicrometer Metallic Barcodes" *Science* 294:137-141 (2001).

Nie and Emory, "Probing Single Molecules and Single Nanoparticles by Surface-Enhanced Raman Scattering" *Science* 275:1102-1106 (1997).

Otto et al., "Surface Enhanced Raman Scattering" *Journal of Physics: Condensed Matter* 4:1143-1212 (1992).

Sche et al., "Display Cloning: Functional Identification of Natural Product Receptors Using cDNA-Phage Display" *Chem Biol*.6:707-716 (1999).

Stadler, "Antibody production without animals" *Dev Biol Stand.* 101:45-48 (1999).

Voldman et al., "Microfabrication in Biology and Medicine" Annu. Rev. Biomed. Engl., 1999, vol. 1, pp. 401-425.

Wittrup, "Phage on display," *Trends Biotechnol.* 1999; 17:423-424.

Xu et al., "Spectroscopy of Single Hemoglobin Molecules by Surface Enhanced Raman Scattering" *Phys. Rev. Lett.* 83:4357-4360 (1999).

Xu et al., "Electromagnetic Contributions to Single-Molecule Sensitivity in Surface-Enhanced Raman Scattering" *Physical Review E.* 62:4318-4324 (2000).

Han, et al., "Quantum-Dot-Tagged Microbeads for Multiplexed Optical Coding of Biomolecules", Nature Biotechnology, vol. 19, Jul. 2001 (pp. 631-635).

\* cited by examiner

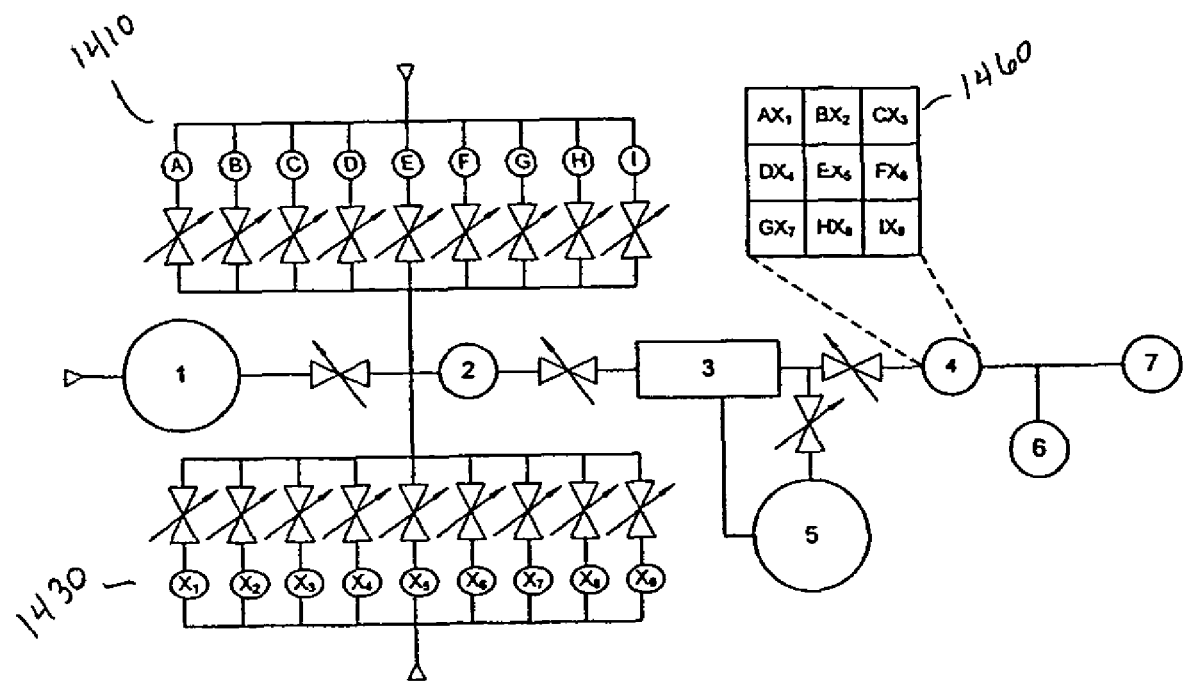
FIG. 14
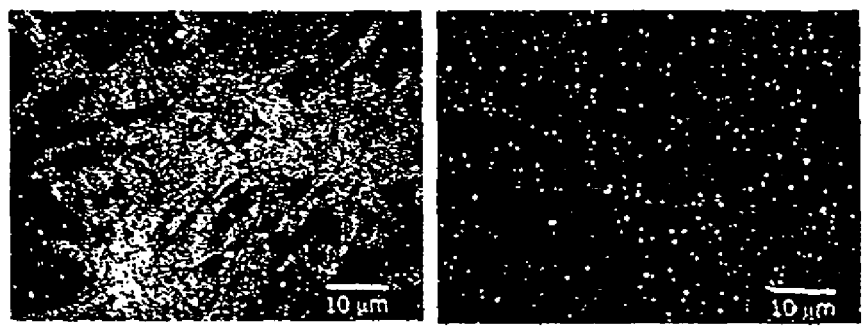
FIG. 15A    FIG. 15B

CELLULAR ANALYSIS USING RAMAN SURFACE SCANNING

This application is a Continuation-in-Part of U.S. Ser. No. 10/927,996, filed Aug. 26, 2004.

BACKGROUND OF THE INVENTION

1. Field of the Invention

The invention relates generally to methods of using nanoparticles for biomolecule analysis, and more specifically to methods of using a composite organic-inorganic nanoparticle (COIN) for detecting and quantitating a molecule by surface-enhanced Raman spectroscopy (SERS), and to methods of using a COIN to image a cell, including one or more molecules in a cell, by SERS.

2. Background Information

Multiplex reactions are parallel processes that exist-naturally in the physical and biological worlds. When this principle is applied to increase efficiencies of biochemical or clinical analyses, the principal challenge is to develop a probe identification system that has distinguishable components for an individual probe in a large probe set. High density DNA chips and microarrays are probe identification systems in which physical positions on a solid surface are used to identify nucleic acid or protein probes. The method of using striped metal bars as nanocodes for probe identification in multiplex assays is based on images of the metal physical structures. Quantum dots are particle-size-dependent fluorescent emitting complexes. Quantum dots, which emit at short wavelength in response to UV excitation, are used for highly multiplexed detection.

Biochips, including DNA arrays (DNA chips), microarrays, protein arrays and the like are devices that may be used to perform highly parallel biochemical reactions. Such devices are fabricated either by building the biomolecules (nucleic acids or proteins) as probes on the chip surface directly or depositing the biomolecules on the chip surface after they have been synthesized. Generally physical positions (XY coordinates) are used to identify the properties or sequences of detected probes molecules.

Conventional cell imaging techniques have used fluorescent dyes. Current research (for example, Jaiswal et al. (2003) *Nature Biotechnology* 12:47-51) has turned to use of quantum dot technology for cell imaging because of their extended lifetime. Also emission spectra from quantum dots are narrower, allowing more colors to be used together. Traditional methods for protein profiling have utilized, for example, two-dimensional gel and MDLC-MS (Multi-dimensional Liquid Chromatographs-Mass Spectroscopy).

The ability to detect and identify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-selective spectrometer in which a detector converts the energy of impinging photons to electrical signal intensity.

Among many analytical techniques that may be used for chemical structure analysis, Raman spectroscopy is attractive for its capability in providing rich structure information from a small optically focused area or detection cavity. Compared to a fluorescent spectrum that normally has a single peak with half peak width of tens of nanometers (quantum dots) to hundreds of nanometers (fluorescent dyes), a Raman spectrum has multiple bonding-structure-related peaks with half peak width of as small as a one nanometer, or less. Surface enhanced Raman scattering (SERS) techniques make it possible to obtain a $10^6$ to $10^{14}$ fold Raman signal enhancement, and may allow for single molecule detection sensitivity. Such huge enhancement factors are attributed primarily to enhanced electromagnetic fields on curved surfaces of coinage metals. Although the electromagnetic enhancement (EME) has been shown to be related to the roughness of metal surfaces or particle size when individual metal colloids are used, SERS is most effectively detected from aggregated colloids. Chemical enhancement may also be obtained by placing molecules in a close proximity to the surface in certain orientations. Due to the rich spectral information and sensitivity, Raman signatures have been used as probe identifiers to detect a few attomoles of molecules when SERS method was used to boost the signals of specifically immobilized Raman label molecules, which in fact are the direct analytes of the SERS reaction. The method of attaching metal particles to Raman-label-coated metal particles to obtain SERS-active complexes has also been studied. A SERS signal also may be generated after attaching thiol-containing dyes to gold particles followed silica coating.

Analyses for numerous chemicals and biochemicals by SERS have been demonstrated using: (1) activated electrodes in electrolytic cells; (2) activated silver and gold colloid reagents; and (3) activated silver and gold substrates. However, none of the foregoing techniques is well suited for providing quantitative measurements. Consequently, SERS has not gained widespread use. In addition, many biomolecules such as proteins and nucleic acids do not have unique Raman signatures because these types of molecules are generally composed of a limited number of common monomers.

SERS technique has become an important analytical tool because it may identify and detect single molecules without labeling. SERS effect is attributed mainly to electromagnetic field enhancement and chemical enhancement. It has been reported that silver particle sizes within the range of 50-100 nm are most effective for SERS. Theoretical and experimental studies also reveal that metal particle junctions are the sites for efficient SERS.

DESCRIPTION OF THE FIGURES

FIG. 14 illustrates a microfluidic array assembly for fabricating COIN-probe conjugates.

FIG. 15A provides an optical image of cells immobilized on an array and FIG. 15B provides a control image of an array in which there are no cells in the culture medium).

DETAILED DESCRIPTION OF THE INVENTION

Figure 1:
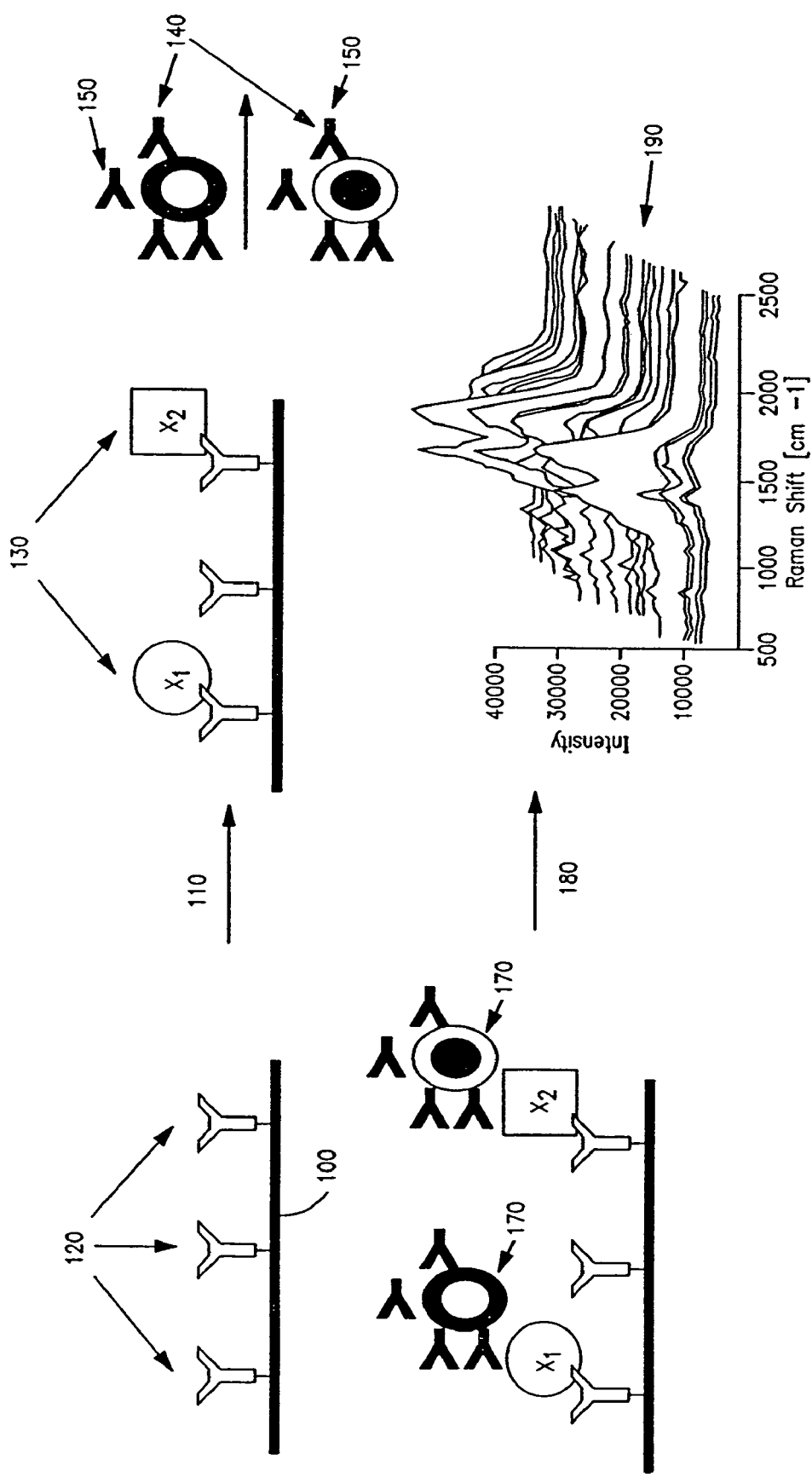
FIG. 1 is a flow diagram illustrating an invention antibody sandwich assay using a composite organic-inorganic nanoparticle (COIN).

Referring to FIG. 1, a flow diagram of a two-step sandwich assay in accordance with one or more embodiments of the invention is exemplified. The invention methods for performing a protein binding assay without signal amplification include contacting a biological sample 110 with a substrate 100 having a set of capture antibodies 120 that bind specifically to different proteins attached at defined locations on the substrate 100 to allow formation of antibody-protein complexes 130. The antibody-protein complexes are then contacted with a set of COIN-labeled probes 140 comprising a probe moiety 150 that binds specifically to a known protein analyte and a COIN 160 comprising at least one distinguishable Raman-active compound so as to form analyte-COIN complexes 170. After removal of unbound COIN-labeled probes from the array, the array may be scanned 180 to detect in multiplex fashion SERS signals 190 at the defined locations, to identify the presence of the known proteins in the biological sample without signal amplification.

In one aspect of the invention sandwich assay, the capture antibody attached to the substrate (for example in an array of defined locations) can be incorporated into a probe-labeled COIN so that captured analyte-COIN complexes 170 will contain at least two COIN and thereby deliver an increased SERS signal upon irradiation of the captured complex. The COIN may include several fused or aggregated primary metal crystal particles with Raman-active organic compounds adsorbed on the surface, in the junctions of the primary particles or embedded in the crystal lattice of the primary metal particles, with any of the Raman-active organic compounds adsorbed on the exterior of the COIN generally being less Raman-active than if situated between metal surfaces or metal atoms. COIN-labeled probes intrinsically produce SERS signals, thus making them suitable, for example, in methods for assaying biological molecules, most of which generate only a weak Raman signal.

In a version of a sandwich protein detection assay such as that exemplified in FIG. 1, protein binding may be detected through both specific antibody binding and degenerate antibody binding if the SERS signal detector has spatial resolution of less than about 5 microns. Thus high resolution is needed to distinguish degenerate binding by semi-specific interaction between the molecules in the complexes formed from specific binding. Degenerate binding is useful for identifying proteins with similarly shaped epitopes.

Figure 2:
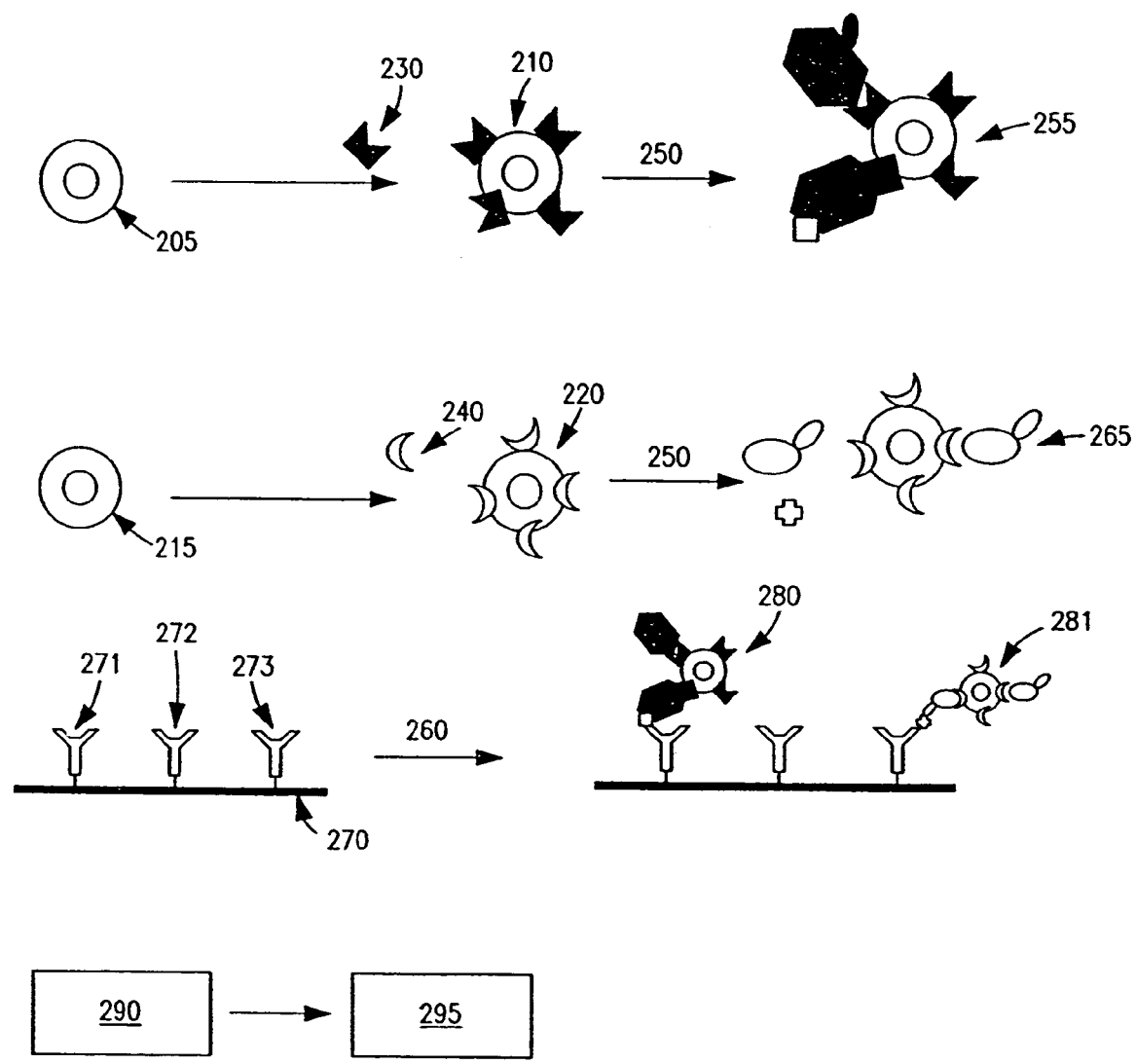
FIG. 2 is a flow diagram illustrating an invention direct binding assay for protein profiling based on binding of biomolecules to known capture antibody and distinguishable COIN signatures from probe-COIN conjugates.

Referring to FIG. 2, a flow diagram of an assay of a biological sample in accordance with one or more embodiments of the invention will be discussed. At least two types of COIN-labeled probes 210, 220 may be used, wherein a COIN 205, 215 includes a probe 230, 240 that binds to a specific known protein-entraining molecule. A protein-entraining molecule as the term is used herein is one found in high abundance in biological samples, such as blood serum, and which in its in vivo environment naturally entrains or associates with smaller proteins and protein fragments. Examples of such protein-entraining molecules are protein G, immunoglobulin G (IgG), immunoglobulin A (IgA), and albumin.

The COINs 210, 220 in the COIN-labeled probes of a set also may comprise one or more Raman-active organic compounds selected to produce a distinguishable Raman signal associated with the particular protein-entraining molecule to which the probe binds. The biological sample 250 is contacted with the COIN-labeled probes 210, 220 in solution under conditions suitable to allow binding of the probe moieties of the COIN-labeled probes to the protein-entraining molecules in the sample to form Raman-active complexes 255, 265. An array 270 having two or more defined locations with two or more capture probes 271, 272, 273 of different specificity attached at defined locations is then contacted with sample 260, containing the Raman-active complexes 255, 265 formed as described above. The contacting is under conditions suitable to form immobilized complexes 280, 281 (for example, immobilized capture probe-protein-entraining molecule-entrained protein target complexes). After removal of unbound reaction components, SERS signatures emitted by the immobilized COIN-containing complexes are detected 290 and particular SERS signatures emitted from complexes immobilized on the array are associated with the presence in the sample of protein targets 290 characterized by either specific 280 or degenerate 281 simultaneous binding to a particular known carrier protein and to a known capture probe. In one aspect, the COIN-labeled probes have two or more of the appropriate COIN embedded within a polymer microsphere (see FIGS. 9-13) and the probe moiety is attached to the polymer microsphere (for example, to the surface of the microsphere using techniques described herein).

In another aspect, the capture probes used to immobilize complexes from the sample may be antibodies of known specificity attached at different known defined locations on the array. In this case, detection further involves collecting position-associated SERS signals from the immobilized complexes at the known locations and correlating the position-associated SERS signals with the specificity of the capture antibodies to characterize the target protein immobilized at a particular location. The invention methods for assaying a biological sample may be used to construct a protein profile of the target proteins in the sample based on degenerate binding of the target proteins with capture probes and protein-entraining molecules. In various embodiments, the biological sample used is blood serum or another bodily fluid such as disclosed herein or otherwise known and routinely used in the art.

Figure 3:
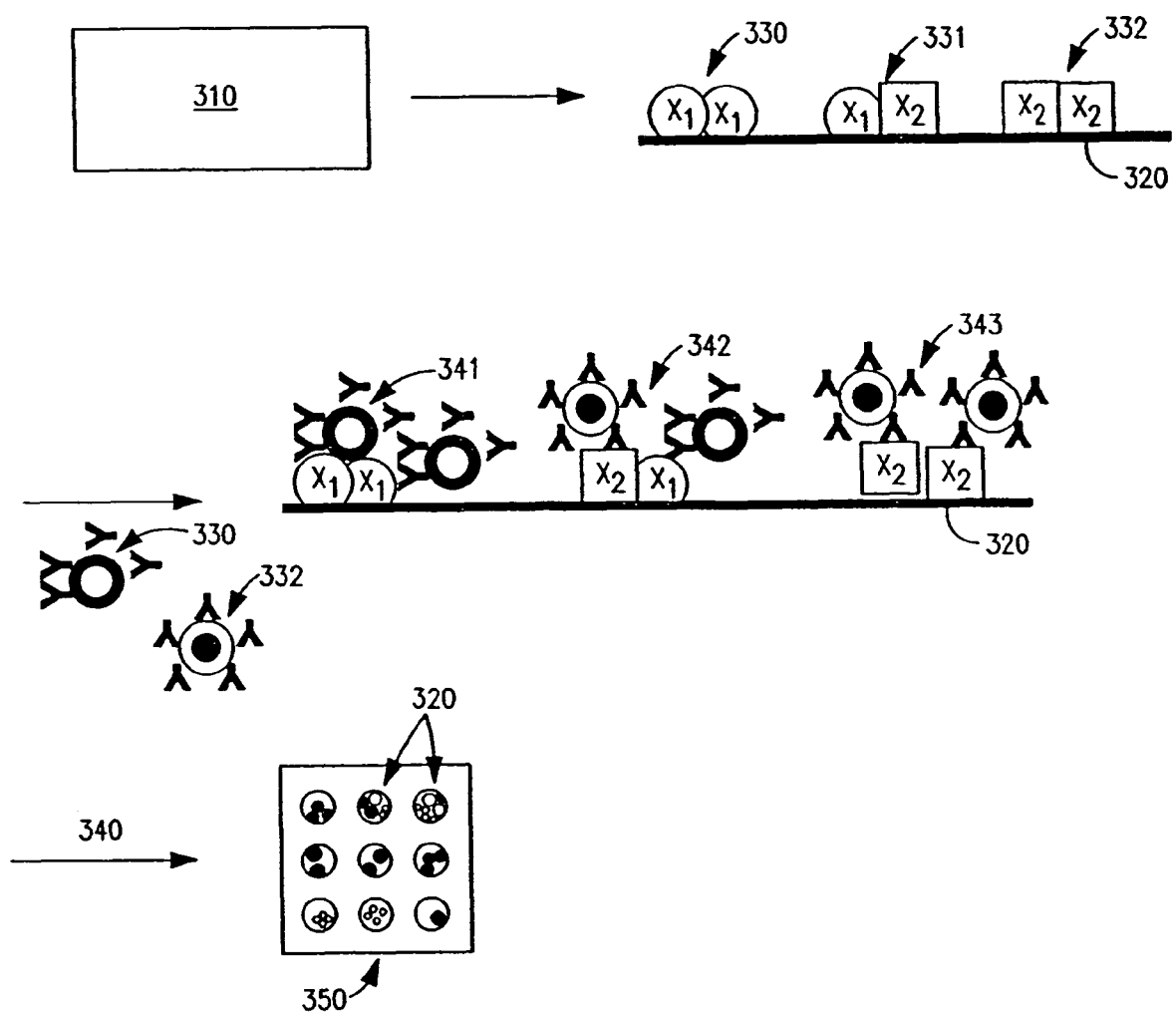
FIG. 3 is a flow diagram illustrating an invention reverse phase array for creating a protein profile based on distinguishable SERS signals obtained from biomolecules at different position-addressable microarray locations.

Referring to FIG. 3, a flow diagram of a reverse phase assay of tissue samples in accordance with one or more embodiments of the invention will be discussed. The invention reverse phase protein assay includes forming one or more arrays of cell lysates obtained from one or more tissue samples from a patient. For example, individual cells of a cell population obtained from a patient tissue sample may be lysed and extracted 310 to form an array. If cell lysates are obtained from more than one tissue sample, two or more arrays may be formed, with an array containing the cell lysates from a particular tissue sample of the patient In an array of defined locations 320 on a substrate, a mixture of extracted cell proteins 330, 331, 332 is immobilized at (for example, spotted onto) individual defined locations, which have been pre-derivatized with capture molecules to capture proteins from the mixture of protein molecules at the defined locations thereon. Then the cell lysate spots at the defined locations are contacted with a mixture of COIN-labeled probes 330, 332 under conditions suitable to form analyte-COIN complexes 341, 342, 343 as the probes bind individual proteins in the spots through both specific and degenerate binding. After removal of unbound COIN-labeled probes from the array, the array 350 may be scanned 340 to detect SERS signals at the defined locations 320 so as to identify and compile data regarding the presence of the known analytes in the tissue sample.

In one aspect, the invention method utilizes a disease-associated tissue sample obtained from a patient and the probe moiety is selected to bind specifically to a protein analyte associated with the disease for which the probe is selected, for example a disease marker protein. In another aspect, the invention method employs two or more arrays with a single array having immobilized proteins from a different one of the tissue samples from the patient. For instance, tissue samples may be collected from tissue representing, different stages of disease progression, such tissue representing normal, pre-malignant, invasive, and stromal stages of a tumor progression. In one aspect of the invention, a substrate or chip 350 may be prepared with two or more of the above described arrays on a surface.

In one aspect, these protein arrays are used for screening of molecular markers and pathway targets in patient matched human tissue during disease progression. In contrast to previous protein arrays that immobilize the probe, in the invention reverse phase protein array methods the whole repertoire of patient proteins that represent the state of individual tissue cell populations undergoing disease transitions are immobilized at defined locations on a functionalized substrate suitable for use in multiplex SERS detection as described herein. A high degree of sensitivity, precision and linearity may be achieved, making it possible to quantify disease progression, for example, the phosphorylated status of signal proteins in human tissue cell subpopulations.

The invention reverse phase protein profiling methods may be used, for example, to observe longitudinal analyses of the state of proteins at the microscopic transition stage from patient matched histologically normal prostate epithelium to prostate intraepithelial neoplasia (PIN), and then to invasive prostate cancer. The activated (for example, phosphorylated) state of signal pathway checkpoints in vivo may be a determinant of diseased cellular physiology, such as early stage cancer. It is also known that in glandular tissue such as breast and prostate, malignant neoplasia originates in microscopic lesions, which evolve over time. Stationary flat epithelium and myoepithelium, is replaced by the piling up of multiple layers of neoplastic cells within the duct or gland lumen. As time proceeds, there is a transition to invasive carcinoma. A hallmark of invasion is disruption of the periglandular basement membrane, and the migration of neoplastic cells into the surrounding stroma.

Consequently, the invention reverse phase protein array methods offer an efficient means to analyze the subtle quantitative changes in multiple classes of proteins taking place substantially simultaneously within an individual cell type by analyzing proteins extracted from whole cell lysates. Such changes may show the slow progression of precancerous lesions over many years. In particular, changes in the activation status of signal pathway circuits that regulate downstream cell cycle progression and pro-survival may generate an imbalance, which ultimately results in the loss of cell growth control and the net accumulation of neoplastic cells.

The invention reverse phase protein array methods may also be used to immobilize whole protein lysates from histopathologically relevant cell populations procured, for example, by Laser Capture Microdissection (LCM) to capture various stages of microscopic progressing cancer lesions within individual patients. In contrast to antibody arrays, ligand arrays, or heterogeneous tissue fragment arrays, the protein arrays used in the invention methods contain immobilized proteins from pure microdissected human tissue cells, which may be used to analyze the state of marker proteins (for example, indicators of checkpoints for pro-survival and growth regulation) to monitor transition from histologically normal epithelium to invasive carcinoma with high precision, specificity and dynamic range.

The invention protein microarrays may also be used to track large study sets of protein interactions in parallel similar to the gene expression arrays recently used in functional genomics. In preparation of the arrays for this embodiment of the invention, histopathologically relevant cell populations are microdissected by LCM, lysed in a suitable lysing buffer, and approximately 3 nanoliters of that lysate are arrayed with a pin based microarrayer onto an array on a substrate such as a glass-backed nitrocellulose at defined locations. At an array location a spot is placed that includes the cellular repertoire corresponding to a given pathologic state that has been captured. Subsequently, an array is contacted with at least one COIN-labeled probe that produces a distinctive SERS signal. SERS signals are detected in multiplex fashion by scanning the arrays on the substrate. In the case where a marker protein is the target, a probe moiety, such as an antibody selected to bind specifically to a proteinaceous molecule that is a known diagnostic marker of progression of the disease state to be studied, may be labeled with a COIN or COIN microsphere. For example, two to about four (or more; e.g., 5, 6, 7, etc.) arrays may be used, having immobilized proteins obtained from a particular one of the tissue samples from the patient.

The invention methods of reverse phase protein profiling are broadly applicable to high-throughput molecular analysis of proteomic changes in tissue cells during development of disease, or for monitoring disease after treatment. Those of skill in the art will be aware that genomic and proteomic initiatives are yielding growing catalogs of disease associated proteins, and thereby constitute candidates for diagnostic or therapeutic targets.

Figure 4:
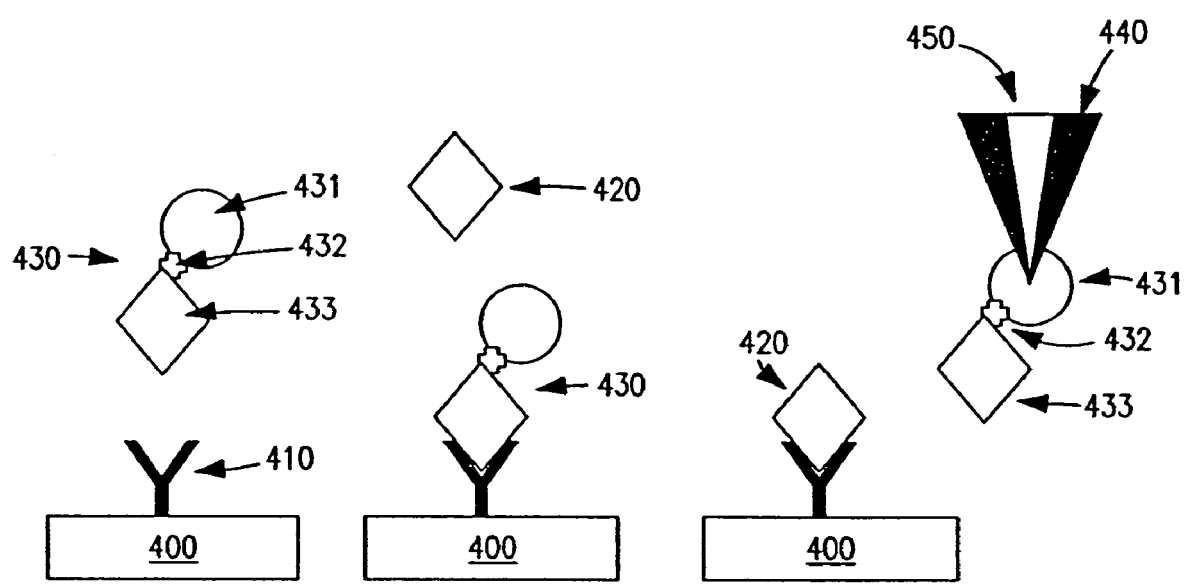
FIG. 4 is a flow diagram illustrating an invention displacement and competitive immunoassay.

Referring to FIG. 4, a flow diagram of a displacement and competitive immunoassay in accordance with one or more embodiments of the invention will be discussed. The invention displacement and competitive immunoassay provides methods for assaying an analyte in a biological sample by contacting together in solution under conditions suitable to allow competitive binding interaction between 1) a substrate 400 having attached to the surface thereof at least one capture probe 410, such as a primary antibody, that binds specifically to a target analyte 420; 2) a known amount of at least one complex of a known antigen 433 specific for capture probe 410, a linker molecule 432, and a COIN 431 comprising at least one Raman active organic compound; and 3) a biological sample containing the target analyte 420. Depending upon the relative concentrations of the target analyte 420 and complex 433, a certain amount of target analyte 420 displaces complex 430 from capture probe 410. The substrate (with any remaining bound capture probe) is optionally removed from contact with the solution. Then, upon radiation with laser beam 450, intensity of at least one SERS signal 450 produced by the COIN-antigen complex 430 freely remaining in the solution (optionally, after removal of the substrate) is detected to determine the amount of the analyte in the sample (for example, by subtracting the amount of complex 430 remaining in the solution from the known amount originally introduced into the solution for interaction therein). In one aspect, the capture probe may be an antibody, such as a monoclonal antibody.

In another aspect, at least 2 up to 1000 or more capture antibodies with different binding specificities may be bound to the substrate surface, known amounts of at least two of the COIN-antigen specific binding complexes containing different antigens that bind respectively to the capture antibodies are used, and intensities of SERS signals are measured in multiplex (for example, using SERS scanning) to determine amounts of at least 2, and up to 1000 or more (e.g., 2, 3, 4, 5, 10, 20, 25, 50, 100, 250, 500, 1000, 1500), analytes in the sample.

Binding with the capture probe may be, for example, by displacement binding or by competition binding by careful selection of the relative binding affinities of the capture probe for the analyte and for the antigen, as is known in the art. For example, if the target molecule is recognized by the substrate bound antibody, the target molecule competes with the COIN-labeled antigen to bind to the antibody. As a result, some of the COIN labeled antigens are released into the solution. By detecting the COIN signal in solution, the amount of released antigen may be measured. Optionally, the solution containing the released COIN may be condensed or further processed to increase the signal. For example, to condense the signal within the solution, the COIN-containing solution may be centrifuged for about 5 min at 10,000×g, or magnetic force may be used to condense the signal within the solution if the COIN contains a paramagnetic compound.

The following non-limiting example illustrates use of the above method. COIN may be labeled with antibodies against prostate specific antigen (PSA). After binding with PSA standards in an immuno-sandwich assay, COIN particles may be released when a sample containing PSA molecules is introduced and contacts the sandwich complexes in solution. The more PSA in the sample, the more COIN will be released into solution. The solution may be condensed by centrifugation as described above prior to detection of SERS signals from COIN in the solution.

In a competitive assay, a known antibody is immobilized on a substrate, the target antigen is mixed with the antigen attached to the COIN, and the mixture of COIN-labeled antigen and target antigen is introduced to the immobilized antibody in solution. If the target antigen is not recognized by the antibody, only the COIN-labeled antigen will bind to the antibody. By detecting the COIN signal in solution, the amount of the residual antigen attached to the COIN is measured. From the amount of the antigen in solution, the binding of the target molecule to the antibody may be calculated. Optionally, the solution containing the released COIN may be condensed as described above to increase the signal.

Since the detection is performed in solution, the number of COIN detected may be higher than is possible with surface detection methods. Also, the effect of non-specific binding is reduced, as the detection is not performed on the array surface. Furthermore, any type of substrate may be used for making the array, as the detection is not performed on the surface of the array.

In another embodiment of the invention methods, COIN-labeled probes are used for staining microstructures within a cell. Accordingly to this embodiment, a set of COIN-labeled probes is utilized, wherein a COIN-labeled probe in the set comprises at least one (e.g., 1, 2, 3, 4, 5, etc.) ligand that binds specifically to a known target microstructure or receptor and one or more Raman-active organic compounds that produce a distinguishable Raman signal. The members of the set of COIN-labeled probes bind to different known target microstructures or receptors. In the assay, the set of probes is introduced into the interior of cells immobilized at discrete locations on an array surface. The COIN-labeled probes may be introduced into the cells using such techniques as endocytosis, transfection, microinjection, and the like. Under suitable conditions, as is known in the art, the COIN-conjugated ligands will bind specifically to receptors and other microstructures within the cells. The COIN stained cells may then be imaged using a scanning Raman microscope to determine the presence in the cells of specific receptors and microstructures. SERS signals from the various distinguishable Raman signals emitted at defined locations on the array may be collected to provide a profile of the microstructures in individual cells and cell types. In addition, it is contemplated to be within the scope of the invention that the profile of a target cell assayed according to the invention methods may be compared with a cell profile similarly obtained from normal cells of the same type to determine the presence of an anomaly in the target cell.

Suitable microstructures for assay using the invention methods include, for example, extracellular matrix molecules such as fibronectin and laminin; intracellular structures such as actin filaments and microtubes; cell nucleus structures such as histone; and the like. Probes suitable for identifying such microstructures are well known in the art and include, for example, antibodies, such as anti-fibronectin antibodies and anti-actin antibodies, and other naturally occurring ligands such as anti-histone protein.

In still another embodiment, a kit for use in the invention methods is provided. The invention kit comprises a chip with at last one array having bound thereto at defined locations a capture molecule that binds to a biological target molecule or cell and a container containing at least one COIN-labeled probe comprising a combination of a known probe moiety and one or more Raman active organic compounds, wherein binding specificity of the probe moiety is correlated with a known Raman signal provided by the Raman active compounds contained in the COIN-labeled probe. The capture molecule may be selected from a probe, such as an antibody or a ligand, or a functional group that forms a complex with a class of biological molecules, such as proteins or nucleic acids. There may also be multiple arrays on a single chip. In an aspect of this embodiment, the array(s) is/are spotted at the defined locations with a multiplicity of antibodies of different specificity. The substrate on which the array is located may be blocked to prevent binding of biological molecules at locations on its surface other than the defined locations. The probe moiety in the COIN-labeled probe may be an antigen to which the antibody binds specifically for use in the competition assay disclosed herein. The invention kits may also provide a set of COIN-labeled probes, for example, in individual containers, the set comprising two or more different known combinations of probe moiety and one or more Raman active organic compounds so as to provide a distinguishable Raman signal when irradiated.

Figure 5:
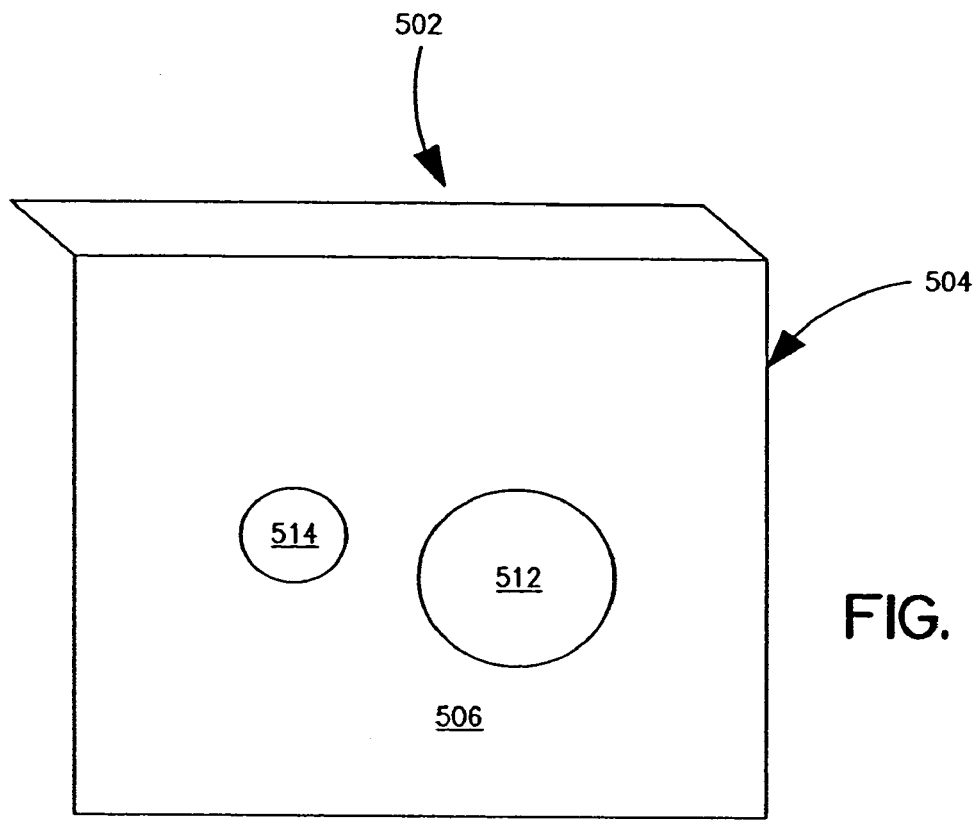
FIG. 5 is a perspective drawing of a top view of an invention displacement immunoassay device.
Figure 6:
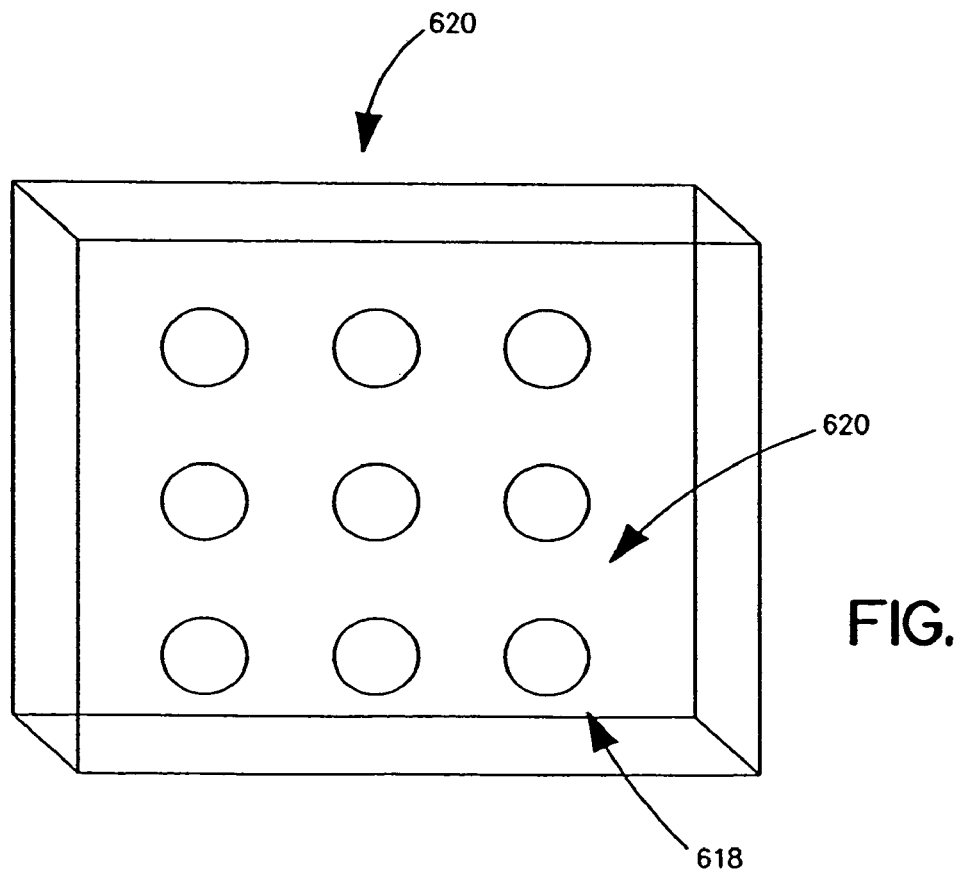
FIG. 6 is a perspective drawing of a frontal view of an invention displacement immunoassay device.
Figure 7:
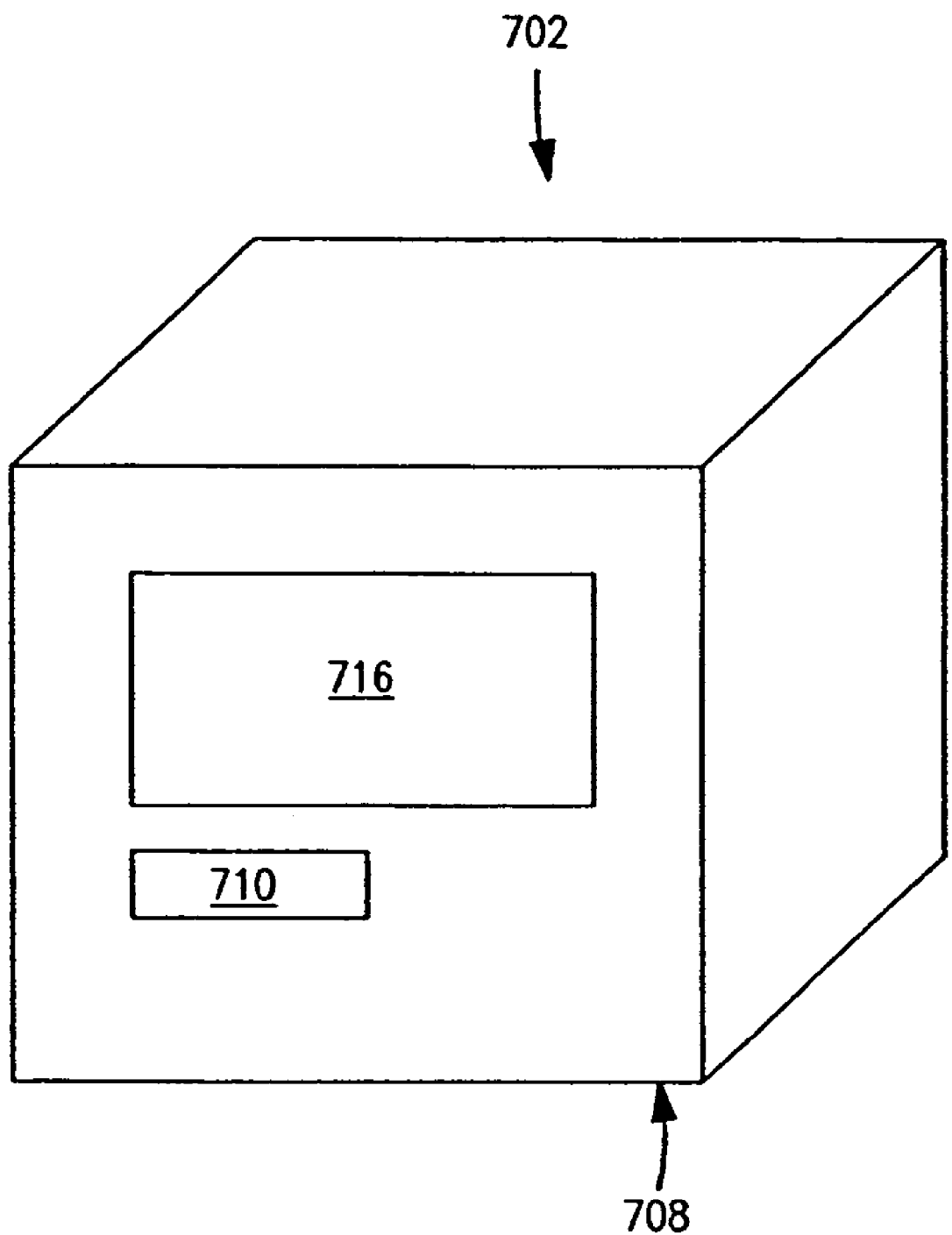
FIG. 7 is a drawing of a chip containing an array of defined locations for attachment of COIN-labeled probes. The chip is inserted into the chip-loading slot of the invention displacement immunoassay device.
Figure 8:
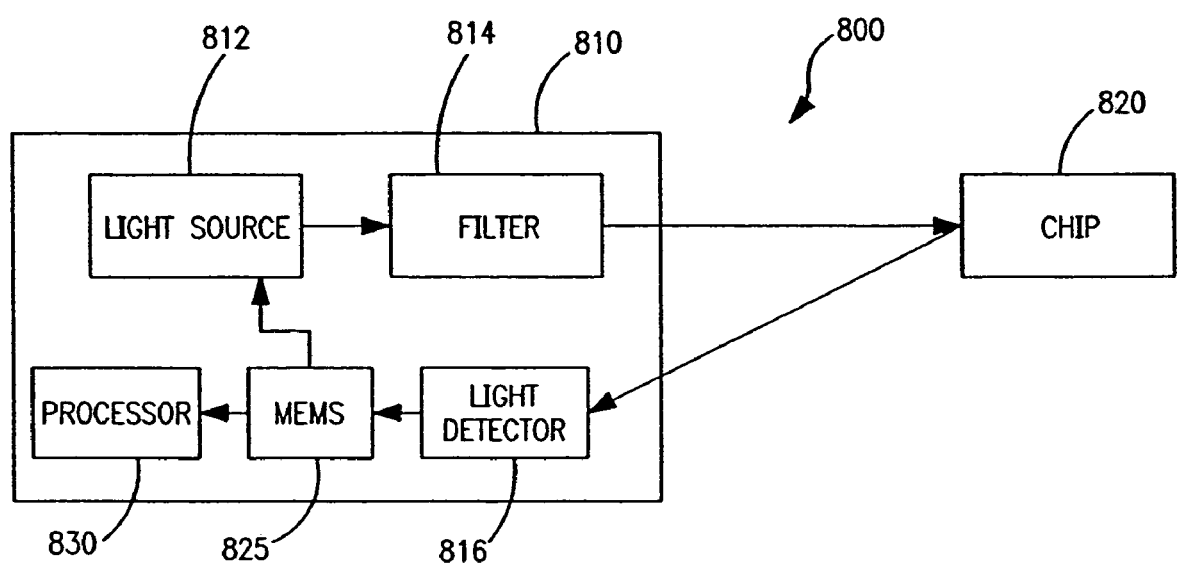
FIG. 8 is a diagram showing components of an apparatus for receiving, detecting and processing a Raman signal.

In another embodiment, the invention provides a system for use in performing the invention displacement assays in solution. As illustrated in FIGS. 5 to 11, the invention system comprises a displacement immunoassay device, which includes a housing having at least two surfaces (for example, 702 and 708; see FIG. 8). A chip loading slot 710 is located in surface 708 for inserting into the device a chip to be assayed. An optional readout display 716 to indicate the results of an assay, such as a light emitting diode display may also be located in surface 708, which is shown as the front of a solid rectangular or square housing (FIG. 7). Referring to FIG. 5, optical window 512 located in surface 508 of the housing is situated in relation to a chip inserted, for example, via the chip loading slot 710 (FIG. 7) so that a beam of light such as that generated by light source 812 (FIG. 8), when situated opposite the optical window 512 is directed onto the top surface of a chip being held in the chip holder. A beam of scattered light from a chip 820 passes to light detector 816 and, via a micro-electro-mechanical system (MEMS) 825, to a processor 830 (FIG. 8). Referring to FIGS. 5 to 7, sample inlet 514 is located in relation to the chip-loading slot 710 such that a liquid sample introduced through the sample inlet 514 (for example, with a syringe) flows directly onto a chip loaded via chip loading slot 710. A buffer solution reservoir 618 mounted on the interior of housing 504 delivers buffer solution to the chip via a tubing running between reservoir 618 and the chip holder for delivering buffer solution to the surface of a chip being held in the chip holder (for example, to promote displacement binding). Conveniently, the sample inlet and optical window may be located in a flat top surface of a square or rectangular housing 504 (as shown in FIGS. 5 and 6) so that a small Raman analyzer 800 may be situated above the top surface of the invention displacement immunoassay device.

The system is designed to hold at least one chip 620 (FIG. 6), which has COIN-labeled probes immobilized at defined locations 618 on chip 620 to form an array on the surface of chip 620. Chip 620 may be prepackaged with buffer solution to preserve activity of probes such as antibodies located on the surface of the chip.

Referring to FIG. 8, when positioned adjacent to immunoassay device 502 Raman analyzer 800 emits a beam of light 822 from a light source 812, which passes through filter 814 and optical window 512 to the surface of chip 820, from which it is reflected back as scattered beam 824. Light detector 816 receives scattered beam 824, filtered through MEMS device 825 and provides a signal representative of a spectrum of the scattered light to processor 830. Raman analyzer 800 may further comprise filter 814 to select a predetermined bandwidth of beam of light 822 directed to chip 820. Chip 620 (FIG. 6) comprises COIN-labeled probes that bind specifically to suspected biomolecules, wherein the COIN-labeled probes are immobilized at defined locations 618 on chip 620. Microconduits running between the defined locations on chip 820 distribute buffer solution to the defined locations 618 to preserve the structure of the probes (for example, antibodies) and promote displacement binding. Binding of a target biomolecule to a probe molecule is detected by the processor 830 (FIG. 8) as a frequency shift in the spectrum of the scatter light beam 824 corresponding to a defined location, which detection is passed on to processor 830.

In certain embodiments of the invention, the metal particles used are formed from metal colloids. As used herein, the term "colloid" refers to a category of complex fluids consisting of nanometer-sized particles suspended in a liquid, usually an aqueous solution. During metal colloid formation or "growth" in the presence of organic molecules in the liquid, the organic molecules are adsorbed on the primary metal crystal particles suspended in the liquid and/or in interstices between primary metal crystal particles. Typical metals contemplated for use in formation of nanoparticles from metal colloids include, for example, silver, gold, platinum, copper, aluminum, and the like. A typical average size range for the metal particles in the colloids used in manufacture of the COINs used in the invention methods and compositions is from about 8 nm to about 15 nm. Such metal colloids may be used to provide metal "seed" particles that are used to generate enlarged metal particles having an average size range from about 20 nm to about 30 nm.

An organic compound (organic molecule) may be any carbon based molecule, and may contain at least one aromatic ring and at least one nitrogen atom. Organic compounds may also contain atoms such as oxygen, sulfur, phosphorus, and the like. As used herein, the term "Raman-active organic compound" refers to an organic molecule that produces a unique SERS signature in response to excitation by a laser. A variety of organic compounds, both Raman-active and non-Raman active, are contemplated for use as components in nanoparticles. In certain embodiments, Raman-active organic compounds are polycyclic aromatic or heteroaromatic compounds. Generally, the Raman-active compound has a molecular weight less than about 500 Daltons.

In addition, it is understood that these Raman-active compounds may be or include fluorescent compounds as well as non-fluorescent compounds. Examples of such compounds include, but are not limited to, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, 9-amino-acridine, and the like.

Additional, non-limiting examples of Raman-active organic compounds include TRIT (tetramethyl rhodamine isothiol), NBD (7-nitrobenz-2-oxa-1,3-diazole), Texas Red™ dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like. These and other Raman-active organic compounds may be obtained from commercial sources (for example, Molecular Probes, Eugene, Oreg.). Chemical structures of exemplary Raman-active organic compounds are shown in Table 1, below. In certain embodiments, the Raman-active compound is adenine, 4-amino-pyrazolo(3,4-d)pyrimidine, or 2-fluoroadenine. In one embodiment, the Raman-active compound is adenine.

When fluorescent compounds are incorporated into nanoparticles as disclosed herein, the compounds may include, but are not limited to, dyes, intrinsically fluorescent proteins, lanthanide phosphors, and the like. Dyes include, for example, rhodamine and derivatives, such as Texas Red™ dye, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow™ dye, IAEDANS, 7-Me2, N-coumarin-4-acetate, 7-OH-4-CH3-coumarin-3-acetate, 7-NH2 -4CH3 -coumarin-3-acetate (AMCA), monobromobimane, pyrene trisulfonates, such as Cascade Blue Yellow™ dye, and monobromotrimethyl-ammoniobimane.

As used herein, the term "distinguishable" means measurably different. As such, a distinguishable Raman signal or Raman signature indicates that individual probes in a set of probes with different binding specificities used in an assay are labeled with COIN, and produce a known, unique Raman signal such that a measurably different Raman signal may be detected. As such, knowledge of the specific binding partner of the attached probe allows for the identification of the presence of the analyte binding partner of the probe in the sample being assayed, including, for example, when the analyte-probe-COIN complex is attached to a solid surface or is in solution. Unique Raman signatures may be created within a set of COIN-labeled probes used in the invention methods by

TABLE 1

| No | Name | Structure |
|----|------|-----------|
| 1 | 8-Aza-Adenine | 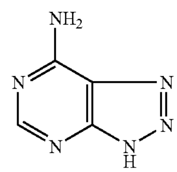 |
| 2 | N-Benzoyladenine | 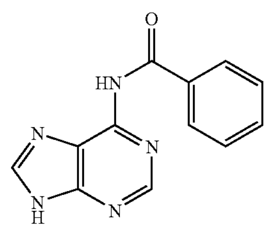 |
| 3 | 2-Mercapto-benzimidazole (MBI) | 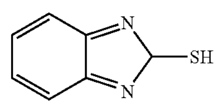 |
| 4 | 4-Amino-pyrazolo[3,4-d]pyrimidine | 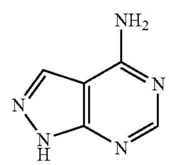 |
| 5 | Zeatin | 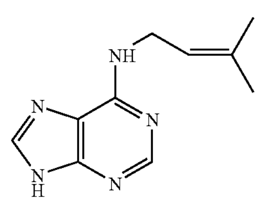 |
| 6 | Methylene Blue | 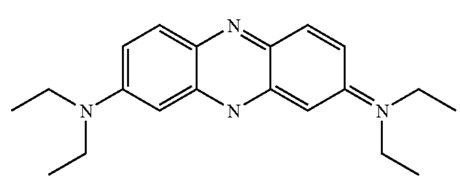 |
| 7 | 9-Amino-acridine | 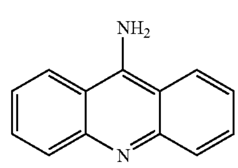 |

TABLE 1-continued
| No | Name | Structure |
|----|------|-----------|
| 8 | Ethidium Bromide | 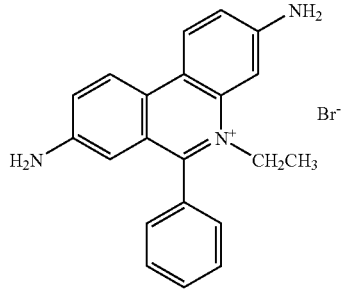 |
| 9 | Bismarck Brown Y | 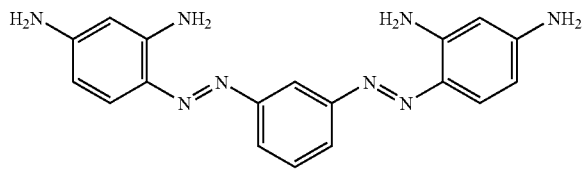 |
| 10 | N-Benzyl-aminopurine | 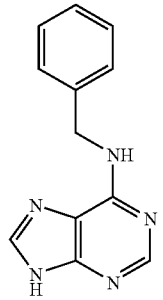 |
| 11 | Thionin acetate | 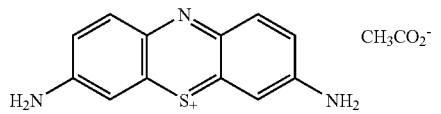 |
| 12 | 3,6-Diaminoacridine | 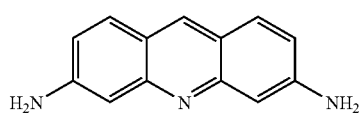 |
| 13 | 6-Cyanopurine | 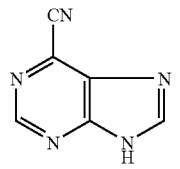 |
| 14 | 4-Amino-5-imidazole-carboxamide hydrochloride | 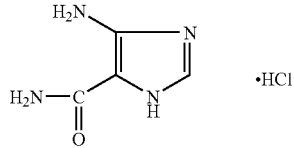 |
| 15 | 1,3-Diiminoisoindoline | 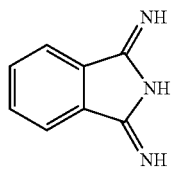 |

TABLE 1-continued

| No | Name | Structure |
|---|---|---|
| 16 | Rhodamine 6G | R6G |
| 17 | Crystal Violet | 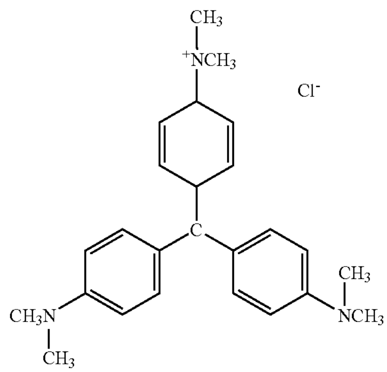 |
| 18 | Basic Fuchsin | 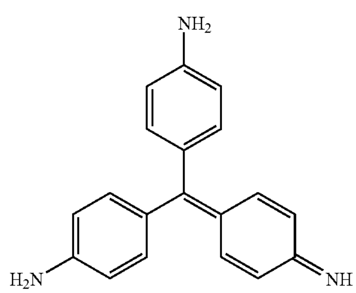 |
| 19 | Aniline Blue diammonium salt | 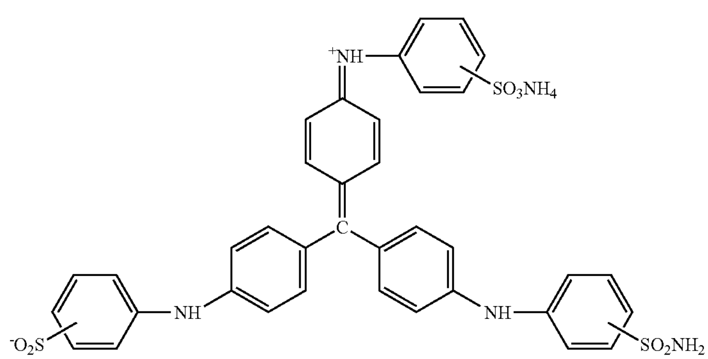 |
| 20 | N-[(3-(Anilinomethylene)-2-chloro-1-cyclohexen-1-yl)methylene]aniline monohydrochloride | 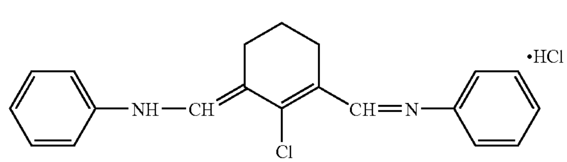 |

TABLE 1-continued

| No | Name | Structure |
|----|------|-----------|
| 21 | O-(7-Azabenzotriazol-1-yl)-N,N,N',N'-tetramethyluronium hexafluorophosphate | 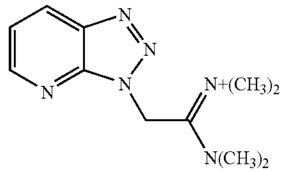 |
| 22 | 9-Aminofluorene hydrochloride | 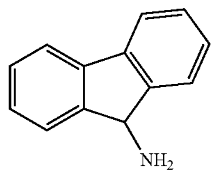 |
| 23 | Basic Blue | 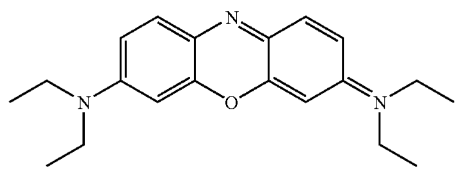 |
| 24 | 1,8-Diamino-4,5-dihydroxyanthraquinone | 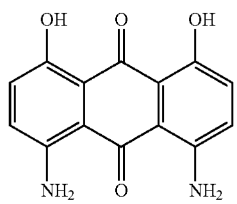 |
| 25 | Proflavine hemisulfate salt hydrate | 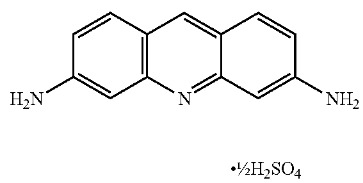 |
| 26 | 2-Amino-1,1,3-propenetricarbonitrile | 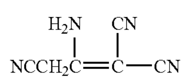 |
| 27 | Variamine Blue RT Salt | 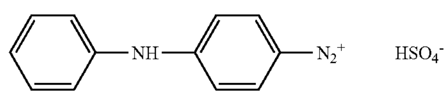 |
| 28 | 4,5,6-Triaminopyrimidine sulfate salt | 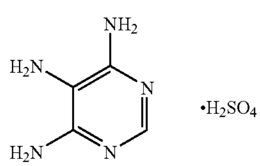 |
| 29 | 2-Amino-benzothiazole | 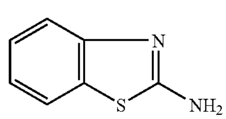 |
| 30 | Melamine | 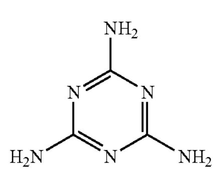 |

TABLE 1-continued

| No | Name | Structure |
|----|------|-----------|
| 31 | 3-(3-Pyridylmethylamino)propionitrile | 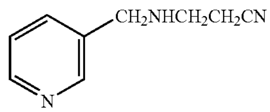 |
| 32 | Silver(I) sulfadiazine | 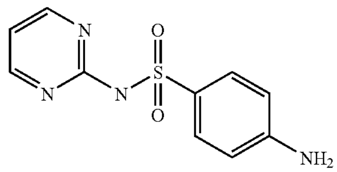 |
| 33 | Acriflavine | |
| 34 | 4-Amino 6-Mercaptopyrazolo[3,4-d]pyrimidine | 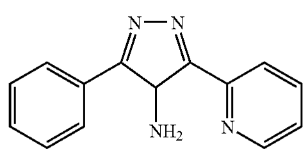 |
| 35 | 2-Am-Purine | 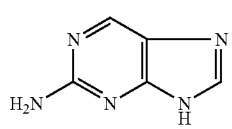 |
| 36 | Adenine Thiol | 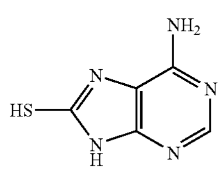 |
| 37 | F-Adenine | 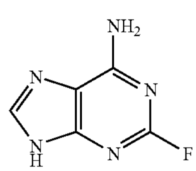 |
| 38 | 6-Mercaptopurine | 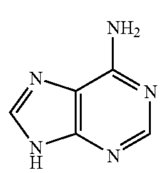 |
| 39 | 4-Amino-6-mercaptopyrazolo[3,4-d]pyrimidine | 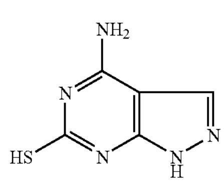 |

TABLE 1-continued

| No | Name | Structure |
|---|---|---|
| 41 | Rhodamine 110 | 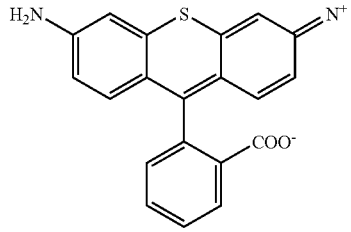 | using different Raman labels, different mixtures of Raman labels and different ratios of Raman labels for labeling individual probes in a set of probes. High sensitivity of the invention assay methods is achieved by incorporating many, indeed up to thousands, of Raman label molecules in a single COIN particle.

The term "chip" as used herein refers to a superstructure comprising multiple arrays. For example, a chip may be a substrate containing multiple sub areas corresponding to an array. The arrays may be fluidly isolated by physical barrier structures to created defined locations or the arrays may be in fluid communication to receive the same sample substantially simultaneously or in sequence. The chip and/or the arrays thereon may be in any convenient shape, such as in square, strip and fluid or microfluid channel formats.

COIN are readily prepared using standard metal colloid chemistry. COIN generally are 50 to 200 nanometers (nm) in average diameter and may be aggregated together in a COIN polymer bead, referred to herein as a "microsphere", which has an average diameter in the range from about 1 micrometer to about 5 micrometers. COIN particles are less than 1 micrometer in size, and are formed by particle growth in the presence of organic compounds. The preparation of such nanoparticles also takes advantage of the ability of metals to adsorb organic compounds. Indeed, since Raman-active organic compounds are adsorbed onto the metal during formation of the metallic colloids, many Raman-active organic compounds may be incorporated into a nanoparticle without requiring special attachment chemistry. In certain embodiments, primary COINs (for example, less than 60 nm) are aggregated to form stable clustered structures that range in size from about 35 nm to about 200 nm, for example, about 50 nm to about 200 nm.

The COIN used COIN-labeled probes in invention methods are prepared by a physico-chemical process called Organic Compound Assisted-Metal Fusion (OCAMF) also called organic compound-induced particle aggregation and coalescence (PAC). In SERS, the Raman signal enhancement may be attributed primarily to an increase in the electromagnetic field on curved surfaces of coinage metals. Chemical enhancement (CE) may be obtained by placing molecules in a close proximity to metal surfaces. Theoretical analysis predicts that electromagnetic enhancement (EME) is particularly strong on rough edges of metal particles.

The composite organic-inorganic nanoparticles (COIN) are used as labels (or reporters) for various types of probes both for proteinaceous molecules and for nucleotide sequences. According to the COIN concept, the interaction between the organic Raman label molecules and the metal colloids has mutual benefits. Besides serving as signal sources, the organic molecules promote and stabilize metal particle association that is in favor of EME of SERS. On the other hand, the metal atoms or the metal crystal structures provide spaces to hold and stabilize Raman label molecules, especially those in the junction between primary metal crystal particles in a cluster of such particles.

In general, COINs may be prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. This type of nanoparticle is a cluster of several primary metal crystal particles with the Raman-active organic compound trapped in the junctions of the primary particles or embedded in the metal atoms. The COIN are not usually spherical and often include grooves and protuberances. COIN may typically be isolated by membrane filtration. In addition, COIN of different sizes may be enriched by centrifugation.

In another aspect, the COIN may include a second metal different from the first metal, wherein the second metal forms a layer overlying the surface of the COIN. To prepare this type of nanoparticle, COIN are placed in an aqueous solution containing suitable second metal cations and a reducing agent. The components of the solution are then subjected to conditions that reduce the second metallic cations, thereby forming a metallic layer overlying the surface of the nanoparticle. In certain embodiments, the second metal layer includes metals, such as, for example, silver, gold, platinum, aluminum, copper, zinc, iron, and the like. This type of nanoparticle may be isolated and/or enriched in the same manner described above.

In certain embodiments, the metallic layer overlying the surface of the nanoparticle is referred to as a protection layer. This protection layer contributes to aqueous stability of the colloidal nanoparticles. As an alternative to a metallic protection layer, or in addition to metallic protection layers, COINs may be coated with a layer of silica. If the COIN have been coated with a metallic layer, for example, gold, a silica layer may be attached to the gold layer by vitreophilization of the COIN with, for example, 3-aminopropyltrimethoxysilane (APTMS). Silica deposition is initiated from a supersaturated silica solution, followed by growth of a silica layer by drop-wise addition of ammonia and tetraethyl orthosilicate (TEOS). The silica-coated COIN are readily functionalized using standard silica chemistry. In alternative embodiments, titanium oxide or hematite may be used as a protection layer.

In another embodiment, COIN may include an organic layer overlying the metal layer or the silica layer. Typically, this type of COIN is prepared by covalently attaching organic compounds to the surface of the metal layer in a type II COIN. Covalent attachment of an organic layer to the metallic layer may be achieved in a variety ways well known to those skilled in the art, for example, through thiol-metal bonds. In alternative embodiments, the organic molecules attached to the metal layer may be crosslinked to form a solid molecular network coating. An organic layer may also be used to provide colloidal stability and functional groups for further derivatization of the COIN, such as attachment of a probe moiety.

An exemplary organic layer is produced by adsorption of an octylamine modified polyacrylic acid onto the COIN, the adsorption being facilitated by the positively charged amine groups. The carboxylic groups of the polymer are then crosslinked with a suitable agent such as lysine, (1,6)-diaminoheptane, and the like. Unreacted carboxylic groups may be used for further derivation. Other functional groups may be also introduced through the modified polyacrylic backbones. The functional groups may be used for attachment of the COIN to the surface of a substrate and to attach probes to the COIN.

Attachment of a probe to or inclusion of a probe in the organic layer is especially useful in the detection of biological molecules. In certain embodiments, exemplary probes are antibodies, antigens, polynucleotides, oligonucleotides, receptors, ligands, and the like. In other embodiments, the organic layer may include a polynucleotide probe.

The probes attached to or incorporated into organic surface molecules of the COIN may be selected to bind specifically to molecular epitopes, for example, receptors, lipids, peptides, cell adhesion molecules, polysaccharides, biopolymers, and the like, presented on the surface membranes of cells or within the extracellular matrix of biomolecular analytes or to oligonucleotide sequences. A wide variety of probes, including but not limited to antibodies, antibody fragments, peptides, small molecules, polysaccharides, nucleic acids, aptamers, peptidomimetics, and oligonucleotides, alone or in combination, may be utilized to specifically bind to cells, cellular epitopes and/or receptors contained in analytes of interest in biological samples. These probes may be attached to a COIN surface or derivatized COIN surface covalently (direct-conjugation) or noncovalently (indirect conjugation).

Avidin-biotin specific binding partners are extremely useful noncovalent systems that have been incorporated into many biological and analytical systems. Avidin has a high affinity for biotin (approximately $10^{-15}$ M), facilitating rapid and stable binding under physiological conditions. Attachment of one or more probes to a single COIN, as described herein, may be accomplished utilizing this approach in two or three steps, depending on the formulation, to complete the COIN-avidin-probe "sandwich". In fact, the COIN surface may be decorated with a multiplicity of probe molecules using this technique. Alternatively, avidin, with four, independent biotin binding sites provides the opportunity for attachment of multiple COIN having biotin surface molecules to an avidin-derivatized "defined location" (for example, spot) on a substrate surface, as disclosed herein.

Targeting probes may be chemically attached to the surface organic coating of COIN by a variety of methods known in the art and as described herein, depending upon the nature of the probe and composition of organic surface molecules of the COIN. A "probe" is a molecule that binds to another molecule. As used herein, the term "probe" generally refers to a small targeting molecule that binds specifically to another molecule on a biological surface separate and distinct from the COIN itself. Such a binding reaction does not require, nor exclude, a molecule that donates or accepts a pair of electrons to form a coordinate covalent bond with a metal atom of a coordination complex. Conjugations may be performed before or after an organic coating is applied to the COIN, depending upon the probe employed. Direct chemical conjugation of probes to proteinaceous molecules often takes advantage of numerous amino-groups (for example lysine) inherently present within the surface.

Another common post-processing approach is to activate surface carboxylates with carbodiimide prior to probe addition. The selected covalent linking strategy is primarily determined by the chemical nature of the probe. Monoclonal antibodies and other large proteins may denature under harsh processing conditions; whereas, the bioactivity of carbohydrates, short peptides, nucleic acids, aptamers, or peptidomimetics often may be preserved. To promote high probe binding integrity and increase avidity for the organic molecule of the COIN, flexible polymer spacer arms, for example polyethylene glycol, amino acids or simple caproate bridges, may be inserted between an activated surface functional group and the probe. These extensions may be 10 nm, or longer, and minimize interference of probe binding by COIN surface interactions.

In various embodiments, the organic layer in the COIN has an antibody, or fragment thereof as a probe moiety. As used herein, the term "antibody" is used in its broadest sense to include polyclonal and monoclonal antibodies, as well as antigen binding fragments (e.g., Fab fragments) of such antibodies, and single chain antibodies. An antibody useful in a method of the invention, or an antigen-binding fragment thereof, is characterized, for example, by having specific binding activity for an epitope of an analyte.

The antibody probe conjugated with a COIN or attached to a substrate as a capture probe includes, for example, naturally occurring antibodies as well as non-naturally occurring antibodies, including, for example, single chain antibodies, chimeric, bifunctional and humanized antibodies, as well as antigen-binding fragments thereof. Such non-naturally occurring antibodies may be constructed using solid phase peptide synthesis, may be produced recombinantly or may be obtained, for example, by screening combinatorial libraries consisting of variable heavy chains and variable light chains. These and other methods of making, for example, chimeric, humanized, CDR-grafted, single chain, and bifunctional antibodies are well known to those skilled in the art.

The term "binds specifically" or "specific binding activity," when used in reference to an antibody means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, F(ab')2, Fd and Fv fragments of an antibody that retain specific binding activity for an epitope of an antigen, are included within the definition of an antibody.

In the context of the invention, the term "ligand" denotes a naturally occurring specific binding partner of a receptor, a synthetic specific-binding partner of a receptor, or an appropriate derivative of the natural or synthetic ligands. As one of skill in the art will recognize, a molecule (or macromolecular complex) may be both a receptor and a ligand. In general, the binding partner having a smaller molecular weight is referred to as the ligand and the binding partner having a greater molecular weight is referred to as a receptor. A probe may also be a ligand.

Rapid expansion of the monoclonal antibody industry has provided a plethora of antibody probes that may be directed against a wide spectrum of pathologic molecular epitopes. Antibodies or their fragments may be from several classes including IgG, IgM, IgA, IgE or IgD. Immunoglobin-gamma (IgG) class monoclonal antibodies have been most often conjugated to various surfaces to provide active, site-specific targeting. These proteins are symmetric glycoproteins (MW ca. 150,000 daltons) composed of identical pairs of heavy and light chains. Hypervariable regions at the ends of two arms provide identical antigen-binding domains. A variably sized branched carbohydrate domain is attached to complement-activating regions, and the hinge area includes particularly accessible interchain disulfide bonds that may be reduced to produce smaller fragments.

Bivalent $F(ab')_2$ and monovalent F(ab) fragments are derived from selective cleavage of the whole antibody by pepsin or papain digestion, respectively. Elimination of the Fc region greatly diminishes the size of the probe molecule.

Phage display techniques may be used to produce recombinant (for example, human) monoclonal antibody fragments against a large range of different antigens without involving antibody-producing animals. In general, cloning creates large genetic libraries of corresponding DNA (cDNA) chains deducted and synthesized using, for example, reverse transcriptase from total messenger RNA (mRNA) of B lymphocytes. Immunoglobulin cDNA chains are amplified by PCR (polymerase chain reaction) and light and heavy chains specific for a given antigen are introduced into a phagemid vector. Transfection of this phagemid vector into the appropriate bacteria results in the expression of an scFv immunoglobulin molecule on the surface of the bacteriophage. Bacteriophage expressing specific immunoglobulin are selected by repeated immunoadsorption/phage multiplication cycles against desired antigens (for example, proteins, peptides, nuclear acids, and sugars). Bacteriophage strictly specific to the target antigen are introduced into an appropriate vector or host cell (for example, *Escherichia coli*, yeast, cells) and amplified by fermentation to produce large amounts of antibody fragments with structures very similar to natural antibodies. (de Bruin et al., Selection of high-affinity phage antibodies from phage display libraries. *Nat Biotechnol.* 1999; 17:397-399; Stadler, Antibody production without animals. *Dev Biol Stand.* 1999; 101:45-48; Wittrup, Phage on display, *Trends Biotechnol.* 1999; 17:423-424; Sche et al., Display cloning: functional identification of natural product receptors using cDNA-phage display. *Chem Biol.* 1999; 6:(707-716)).

Peptides such as antibodies may have high specificity and epitope affinity for use as COIN probes. These may be small peptides (5 to 10 amino acids) specific for a unique receptor sequences (for example, the RGD epitope of various molecules involved in inflammation) or larger biologically active polypeptides (for example, hormones such as cholecystokinin). Peptides or peptide (nonpeptide) analogues of cell adhesion molecules, cytokines, selectins, cadhedrins, Ig superfamily, integrins and the like may be utilized for COIN probes.

Asialoglycoproteins (ASG) have been used as probes for liver-specific diseases due to their high affinity for ASG receptors located uniquely on hepatocytes. ASG probes have been used to detect primary and secondary hepatic tumors as well as benign, diffuse liver disease such as hepatitis The ASG receptor is highly abundant on hepatocytes, approximately 500,000 per cell, rapidly internalizes and is subsequently recycled to the cell surface. Polysaccharides such as arabinogalactan may also be utilized as probes for hepatic targets. Arabinogalactan has multiple terminal arabinose groups that display high affinity for ASG hepatic receptors.

Aptamers are high affinity, high specificity RNA or DNA-based probes produced by in vitro selection experiments. Aptamers are generated from random sequences of 20 to 30 nucleotides, selectively screened by absorption to molecular antigens or cells, and enriched to purify specific high affinity binding ligands. In solution, aptamers are unstructured but may fold and enwrap target epitopes providing specific binding recognition. The unique folding of the nucleic acids around the epitope affords discriminatory intermolecular contacts through hydrogen bonding, electrostatic interaction, stacking, and shape complementarity. In comparison with protein-based ligands, aptamers are stable and are more conducive to heat sterilization. Aptamers are currently used to target a number of clinically relevant pathologies including angiogenesis, activated platelets, and solid tumors and their use is increasing.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe. Generally, an oligonucleotide useful as a probe or primer that selectively hybridizes to a selected nucleotide sequence is at least 6 nucleotides to about 9 nucleotides in length. Polynucleotide probes used in the invention methods are useful for detecting and hybridizing under suitable conditions to complementary polynucleotides in a biological sample by pairing a known polynucleotide probe with a known Raman-active COIN comprising one or more Raman-active organic compounds, as described herein. A covalent phosphodiester bond generally ligates the nucleotides of a polynucleotide sequence. However, the covalent bond also may be any of numerous other bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs may be particularly useful where the polynucleotide is to be exposed to an environment that may contain a nucleolytic activity, including, for example, a tissue culture medium, since the modified polynucleotides may be less susceptible to degradation.

As used herein, the term "selective hybridization" or "selectively hybridize," refers to hybridization under moderately stringent or highly stringent conditions such that a nucleotide sequence preferentially associates with a selected nucleotide sequence over unrelated nucleotide sequences to a large enough extent to be useful in identifying the selected nucleotide sequence. It will be recognized that some amount of non-specific hybridization is unavoidable, but is acceptable provided that hybridization to a target nucleotide sequence is sufficiently selective such that it may be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (for example, homologous) nucleic acid molecule other than the target nucleic acid molecule. Conditions that allow for selective hybridization may be determined empirically, or may be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing may be carried out using only one of these conditions, for example, high stringency conditions, or a condition may be used, for example, for 10-15 minutes, in the order listed above, repeating any or all of the steps listed. However, as mentioned above, optimal conditions will vary, depending on the particular hybridization reaction involved, and may be determined empirically.

In one embodiment, the invention provides methods for detecting an analyte in a sample, which can be a cell, tissue, or organ sample, or a fraction thereof. Such methods may be performed, for example, by contacting a sample containing an analyte with a COIN including a probe, wherein the probe binds to the analyte; and detecting SERS signals emitted by the COIN, wherein the signals are indicative of the presence of an analyte. In one aspect, the sample includes a pool of biological analytes and the sample is contacted with a set of COINs, as described herein, wherein members of the set are provided with a probe that binds specifically to a known biological analyte and a different combination of Raman-active organic compounds to provide a distinguishable Raman signature, for example, one that is unique to the set, so the Raman signature, when detected, may readily be correlated with the known analyte to which the probe will bind specifically.

By "analyte" is meant any molecule or compound. An analyte, which generally comprises a molecule or compound to be analyzed (for example, detected), may be in the solid, liquid, gaseous, or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase may be changed by pressure, temperature as well as by affecting surface tension of a liquid by the presence or addition of salts, etc.

As indicated above, methods of the present invention, in certain aspects, detect binding of an analyte to a probe that is labeled with a COIN. The analyte may be comprised of a member of a specific binding pair (sbp) and may be a ligand, which is monovalent (monoepitopic) or polyvalent (polyepitopic), usually antigenic or haptenic, and is a single compound or two or more compounds that share at least one common epitopic or determinant site. As such, the analyte may be any of a diverse variety of compositions including, for example, a tissue, a cell, an antibody, a nucleic acid molecule, a cellular polypeptide such as a blood group antigen such as A, B, D, etc., or an HLA antigen, a cellular substructure such as endoplasmic reticulum, a Golgi body, or nuclear membrane, or a microorganism, for example, bacterium, fungus, protozoan, or virus, which can be an intracellular or interstitial parasite of an organism (for example, a human).

A member of a specific binding pair ("sbp member") is one of two different molecules having an area on the surface or in a cavity that specifically binds to and is thereby defined as complementary with a particular spatial and polar organization of the other molecule. Members of a specific binding pair may be referred to as ligand and receptor (antiligand), an analyte and a probe, an antibody and antigen (or epitope), and the like. As such, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs, but are included in the invention and the definition of sbp member.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide hybridization interactions, and so forth. Non-specific binding is non-covalent binding between molecules that is relatively independent of specific surface structures. Non-specific binding may result from several factors, including hydrophobic interactions between molecules.

Specific binding generally occurs between a first binding partner and second binding partner of a pair of specific binding partners. In addition, degenerate binding can occur between a member of a pair of specific binding partners (e.g., a first specific binding partner) and a molecule other than a second binding partner of a pair of specific binding partners. As used herein, "degenerate binding" means the association of a first (or second) binding partner of a specific binding pair with a binding partner other than a specific binding partner. Generally, such an "other" (i.e., degenerate) binding partner has a binding site structure that is similar to a member of a specific binding pair. As such, degenerate binding is semi-specific, and may be exemplified by the crossreactivity of an antibody with a molecule having a similar, but different, structure from that of the antigen (or epitope) to which the antibody specifically binds (e.g., an epitope having one or a few amino acid difference as compared to the antigen specifically bound by an antibody). Degenerate binding may be used to identify one or more (e.g., a set or a group) of molecules that have a structural feature (e.g., an epitope) that is similar to that of a member of a specific binding partner.

The COIN-labeled probes as used in the invention methods may be used to detect the presence of a particular target analyte, for example, a nucleic acid, oligonucleotide, protein, enzyme, antibody or antigen or to screen bioactive agents, for example, drug candidates, for binding to a particular target or to detect the presence of agents, such as pollutants in a soil, water or gas sample. As discussed above, any analyte for which a probe moiety, such as a peptide, protein, oligonucleotide or aptamer, may be designed may be labeled with one or more COINS and used in the invention methods.

The polyvalent ligand analytes will normally be poly (amino acids), for example, polypeptides and proteins, or other protein-containing molecules, nucleic acids, and combinations thereof. Such combinations include components of bacteria, viruses, chromosomes, genes and other nucleic acid sequences, mitochondria, nuclei, cell membranes, cell microstructures, and the like. The term analyte further includes polynucleotide analytes, including, for example, mRNA, rRNA, tRNA, double stranded RNA, DNA, DNA-RNA duplexes, and the like. The term analyte also includes receptors that are polynucleotide binding agents, such as peptide nucleic acids (PNA), restriction enzymes, activators, repressors, nucleases, polymerases, histones, repair enzymes, chemotherapeutic agents, and the like.

The analyte may be a molecule found directly in a sample, such as a body fluid from a host or patient. The sample may be examined directly or may be pretreated to render the analyte more readily detectible. Furthermore, the analyte of interest may be determined by detecting an agent probative of the analyte of interest, such as a specific binding pair member complementary to the analyte of interest, whose presence will be detected only when the analyte of interest is present in a sample. Thus, the agent probative of the analyte becomes the analyte that is detected in an assay. The body fluid may be, for example, urine, blood, plasma, serum, saliva, semen, stool, sputum, cerebral spinal fluid, tears, mucus, and the like. Analytes include nucleic acids, proteins, peptides, lipids, carbohydrates, glycolipids, glycoproteins or any other potential target for which a specific probe may be prepared. An analyte also can be an environmental molecule or a contaminant. For example, the analyte can be an explosive material, and the sample can be dust from a bag of a passenger such as an airline passenger, train passenger, or other passenger of a mass transit system.

The presence of multiple analytes in a sample may be assayed substantially simultaneously, since a member of a set may be distinguishably labeled and detected. Moreover, detection of COIN may be performed in solution or on a surface, with the signal of COIN generally being stronger in solution. COIN in solution may be condensed for further improvement of the detection method. Quantification of the analyte may be performed by standard techniques, well known in spectroscopic analysis. For example, the amount of analyte bound to an invention Raman probe construct may be determined by measuring the signal intensity produced and comparing the signal intensity to a calibration curve prepared from known amounts of similar Raman probe construct standards. Such quantification methods are well within the routine skill in the art.

By "substrate" or "solid support" is meant any material that may be modified to contain defined locations (for example, discrete individual sites) appropriate for the attachment or association of analytes, including cells comprising analytes, or capture probes and amenable to at least one detection method. In general, the substrates are selected to allow or enhance the optical detection method contemplated for use thereon, and do not appreciably interfere with signal emissions.

A substrate useful for the present methods can include such well known devices as chips or microtiter plates, and may comprise a patterned surface containing individual defined locations. Such patterned defined locations may be structured in the form of multiple arrays on a single substrate that may be treated as described herein bind to individual analytes or types of analytes. Alternatively, in embodiments wherein the probe Raman construct is attached to the substrate, a correlation between the location of an individual site on the array and the Raman code or probe located at that particular site may be made. The defined locations comprise a pattern, for example a regular design or configuration, or may be randomly distributed. A regular pattern of sites may be used such that the sites may be addressed in an X-Y coordinate plane. Such an array or substrate is described herein as "position addressable."

A single substrate may provide multiple arrays, for example on a single chip. The size of the array will depend on the end use of the array. Arrays containing from about 2 to many millions of different discrete substrate sites may be made. Generally, the array will comprise from two to as many as a billion or more such sites, depending on the size of the surface. Thus, very high density, high density, moderate density, low density or very low density arrays may be made. Some ranges for very high density arrays are from about 10,000,000 to about 2,000,000,000 sites per array. High density arrays range from about 100,000 to about 10,000,000 sites. Moderate density arrays range from about 10,000 to about 50,000 sites. Low-density arrays are generally less than 10,000 sites. Very low-density arrays are less than 1,000 sites.

The surface of the substrate may be modified to allow attachment of analytes at individual sites. Thus, the surface of the substrate may be modified such that "defined locations", which are discrete sites of binding, are formed. In one embodiment, the surface of the substrate may be modified to contain wells, for example depressions in the surface of the substrate. This may be done using a variety of known techniques, including, but not limited to, photolithography, stamping techniques, molding techniques and microetching techniques. As will be appreciated by those in the art, the technique used will depend on the composition and shape of the substrate. Alternatively, the surface of the substrate may be modified to contain chemically derived sites that may be used to attach analytes or probes to defined locations on the substrate. The addition of a pattern of chemical functional groups, such as amino groups, carboxy groups, oxo groups and thiol groups may be used to covalently attach molecules containing corresponding reactive functional groups or linker molecules.

As disclosed herein, biological analytes may comprise naturally occurring proteins or fragments of naturally occurring proteins. Thus, for example, cells and/or cellular extracts containing proteins, or random or directed digests of proteinaceous cellular extracts, may be used. In this way libraries of procaryotic and eukaryotic cells, and proteins expressed by such cells, may be screened using the systems described herein. For example, pluralities of cells, which may be the same or different, may be used for screening purposes, and/or libraries of bacterial, fungal, viral, and mammalian proteins may be generated for screening purposes.

The biological analytes amenable to examination according to the invention methods also may be peptides of from about 3 to about 30 amino acids or about 5 to about 15 amino acids. The peptides may be digests of naturally occurring proteins or random peptides. Since generally random peptides (or random nucleic acids) are chemically synthesized, they may incorporate any nucleotide or amino acid at any position. The synthetic process may be designed to generate randomized proteins or nucleic acids, to allow the formation of all or most of the possible combinations over the length of the sequence, thus forming a library of randomized biological analytes for screening using the invention methods and constructs.

Alternatively, or in addition, the biological analytes may be nucleic acids. The nucleic acids may be single stranded or double stranded, or a mixture thereof. The nucleic acid may be DNA, genomic DNA, cDNA, RNA or a hybrid, where the nucleic acid includes any combination of deoxyribo- and ribonucleotides, and any combination of bases, including uracil, adenine, thymine, cytosine, guanine, inosine, xanthanine, hypoxanthanine, isocytosine, isoguanine, and base pair analogs such as nitropyrrole and nitroindole, etc.

When a nucleic acid is the target analyte, the probe molecule in the COIN-labeled probe used in the invention methods may be an oligonucleotide. Methods for oligonucleotide synthesis are well known in the art and any such known method may be used. For example, oligonucleotides may be prepared using commercially available oligonucleotide synthesizers (for example, Applied Biosystems, Foster City, Calif.). Nucleotide precursors attached to a variety of tags may be commercially obtained (for example Molecular Probes, Eugene, Oreg.) and incorporated into oligonucleotides or polynucleotides. Alternatively, nucleotide precursors may be purchased containing various reactive groups, such as biotin, diogoxigenin, sulfhydryl, amino or carboxyl groups. After oligonucleotide synthesis, COIN labels may be attached using standard chemistries. Oligonucleotides of any desired sequence, with or without reactive groups for COIN attachment, may also be purchased from a wide variety of sources (for example, Midland Certified Reagents, Midland, Tex.). The oligonucleotide probe is then used to functionalize a COIN particle (for example link a COIN particle to an oligonucleotide probe) using methods disclosed herein, to produce a COIN labeled oligonucleotide probe.

The COIN labeled oligonucleotide probe is used in a hybridization reaction to detect specific binding of the COIN labeled oligonucleotide probe to a target polynucleotide. Alternatively, the COIN labeled oligonucleotide probe may be applied to a reaction mixture that includes the target polynucleotide associated with a solid support, to capture the COIN labeled oligonucleotide probe. The captured COIN labeled oligonucleotide probe may then be detected using Raman spectroscopy, with or without first being released from the solid-support. Detection of the specific Raman label on the captured COIN labeled oligonucleotide probe, identifies the nucleotide sequence of the oligonucleotide probe, which in turn provides information regarding the nucleotide sequence of the target polynucleotide.

In another aspect, COIN labeled aptamers may also be used in practice of the invention methods. "Aptamers" are oligonucleotides derived by an in vitro evolutionary process—the SELEX® process (Brody and Gold, *Mol. Biotechnol.* 74:5-13, 2000). The SELEX® process involves repetitive cycles of exposing potential aptamers (nucleic acid ligands) to a target, allowing binding to occur, separating bound from free nucleic acid ligands, amplifying the bound ligands and repeating the binding process. After a number of cycles, aptamers exhibiting high affinity and specificity against virtually any type of biological target may be prepared. Because of their small size, relative stability and ease of preparation, aptamers may be well suited for use as probes. Since aptamers are comprised of oligonucleotides, they may easily be incorporated into nucleic acid type backbones. Methods for production of aptamers are well known (see, e.g., U.S. Pat. Nos. 5,270,163; 5,567,588; 5,670,637; 5,696,249; 5,843,653). Alternatively, a variety of aptamers against specific targets may be obtained from commercial sources (e.g., Somalogic, Boulder Colo.). Aptamers are relatively small molecules of about 7 to 50 kDa.

The following paragraphs include further details regarding exemplary methods of using COIN-labeled probes (for example, composite organic-inorganic nanoparticles (COIN) that include a probe). It will be understood that numerous additional specific examples of applications that utilize COIN-labeled probes may be identified using the teachings of the present specification. One of skill in the art will recognize that many interactions between polypeptides and their target molecules may be detected using COIN labeled polypeptides. In one group of exemplary applications, COIN labeled antibodies (for example antibodies bound to a COIN) are used to detect interaction of the COIN labeled antibodies with antigens, either in solution or on a solid support (for example, immobilized by a capture antibody). It will be understood that while such immunoassays may be performed using known methods such as, for example, ELISA assays, western blotting, or protein arrays, utilizing the COIN-labeled antibody or COIN labeled secondary antibody, in place of a primary or secondary antibody labeled with an enzyme or a radioactive compound. Such assays differ from conventional assays in that the signal amplification step is unnecessary. In another example, a COIN labeled enzyme is used to detect interaction of the COIN-labeled enzyme with a substrate.

In another embodiment, there are provided systems for detecting an analyte in a sample. Such systems include, for example, an array comprising more than one COIN-labeled probe attached to a substrate at defined locations, nanoparticle; a sample containing at least one analyte; a Raman spectrometer; and a computer including an algorithm for analysis of the sample.

A variety of analytical techniques may be used to analyze the signals produced by irradiation of COIN in the methods described herein. Such techniques include for example, nuclear magnetic resonance spectroscopy (NMR), photon correlation spectroscopy (PCS), IR, surface plasma resonance (SPR), XPS, scanning probe microscopy (SPM), SEM, TEM, atomic absorption spectroscopy, elemental analysis, UV-vis, fluorescence spectroscopy, and the like. In various embodiments, COIN irradiation (excitation) may be performed using electromagnetic radiation in the range of about 260 nm to 1200 nm, including, for example, far ultraviolet light having a wavelength of about 260 to 350 nm (for example, about 325 to 337 nm), visible light having a wavelength of about 350 to 700 nm (for example, about 514 to 532 nm), and infrared light (including near infrared light) having a wavelength of about 700 to 1100 nm.

In the methods of the invention, a "sample" includes a wide variety of cells and/or analytes that may be analyzed using the methods described herein. For example, a sample may be an environmental sample and includes atmospheric air, ambient air, water, sludge, soil, and the like. In addition, in certain embodiments a sample may be a biological sample, including, for example, a cell, which may be a living cells, a subject's breath, saliva, blood, urine, feces, various tissues and biological fluids, and the like.

Commercial applications for the invention methods employing the COIN-labeled probes as described herein include environmental toxicology and remediation, biomedicine, monitoring of food and agricultural products for the presence of pathogens, hospital sanitation monitoring, medical diagnostics, fish freshness, detection and classification of bacteria and microorganisms both in vitro and in vivo for biomedical uses and medical diagnostic uses, ambient air monitoring, worker protection, food product quality testing, leak detection and identification, emergency response and law enforcement applications, forensics, illegal substance detection and identification, enclosed space surveillance, food/beverage/agriculture applications, freshness detection, fruit ripening control, fermentation process monitoring and control applications, flavor composition and identification, product quality and identification, product quality testing, personal identification, air intake monitoring, infectious disease detection and breath applications, body fluids analysis, pharmaceutical applications, drug discovery, , and the like. Another application for the fluid detection methods is in analysis of food quality, halitosis, soil and water contaminants, air quality monitoring, leak detection, fire safety, chemical weapons identification, and use by biohazard material teams, Raman Spectroscopy Raman Detectors In various embodiments of the invention, assays utilizing COIN and microspheres containing multiple COINs may be used in conjunction with known Raman spectroscopy techniques for a variety of applications, such as identifying and/or quantifying one or more analytes in a sample. In the practice of the present invention, the Raman spectrometer may be part of a detection unit designed to detect and quantify nanoparticles of the present invention by Raman spectroscopy. Methods for detection of Raman labeled analytes, for example, nucleotides, using Raman spectroscopy are known in the art (see, for example, U.S. Pat. Nos. 5,306,403; 6,002,471; 6,174,677). Variations on surface enhanced Raman spectroscopy (SERS), surface enhanced resonance Raman spectroscopy (SERRS) and coherent anti-Stokes Raman spectroscopy (CARS) have been disclosed.

A non-limiting example of a Raman detection unit is disclosed in U.S. Pat. No. 6,002,471. An excitation beam is generated by either a frequency doubled Nd:YAG laser at 532 nm wavelength or a frequency doubled Ti:sapphire laser at 365 nm wavelength. Pulsed laser beams or continuous laser beams may be used. The excitation beam passes through confocal optics and a microscope objective, and is focused onto the flow path and/or the flow-through cell. The Raman emission light from the labeled nanoparticles is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics may be used as well as confocal optics. The Raman emission signal is detected by a Raman detector that includes an avalanche photodiode interfaced with a computer for counting and digitization of the signal.

Another example of a Raman detection unit is disclosed in U.S. Pat. No. 5,306,403, including a Spex Model 1403 double-grating spectrophotometer with a gallium-arsenide photomultiplier tube (RCA Model C31034 or Burle Industries Model C3103402) operated in the single-photon counting mode. The excitation source includes a 514.5 nm line argon-ion laser from SpectraPhysics, Model 166, and a 647.1 nm line of a krypton-ion laser (Innova 70, Coherent). Alternative excitation sources include a nitrogen laser (Laser Science Inc.) at 337 nm and a helium-cadmium laser (Liconox) at 325 nm (U.S. Pat. No. 6,174,677), a light emitting diode, an Nd:YLF laser, and/or various ions lasers and/or dye lasers. The excitation beam may be spectrally purified with a bandpass filter (Corion) and may be focused on the flow path and/or flow-through cell using a 6× objective lens (Newport, Model L6x). The objective lens may be used to both excite the Raman-active organic compounds of the nanoparticles and to collect the Raman signal, by using a holographic beam splitter (Kaiser Optical Systems, Inc., Model HB 647-26N18) to produce a right-angle geometry for the excitation beam and the emitted Raman signal. A holographic notch filter (Kaiser Optical Systems, Inc.) may be used to reduce Rayleigh scattered radiation. Alternative Raman detectors include an ISA HR-320 spectrograph equipped with a red-enhanced intensified charge-coupled device (RE-ICCD) detection system (Princeton Instruments). Other types of detectors may be used, such as Fourier-transform spectrographs (based on Michaelson interferometers), charged injection devices, photodiode arrays, InGaAs detectors, electron-multiplied CCD, intensified CCD and/or phototransistor arrays.

Any suitable form or configuration of Raman spectroscopy or related techniques known in the art may be used for detection of the nanoparticles of the present invention, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Micro-Electro-Mechanical Systems (MEMS)

In various embodiments of the invention, the arrays and substrates may be incorporated into a larger apparatus and/or system. In certain embodiments (See FIG. 8), a micro-electro-mechanical system (MEMS) may be incorporated into the system. MEMS are integrated systems comprising mechanical elements, sensors, actuators, pumps and electronics. All of those components may be manufactured by known microfabrication techniques on a common chip, comprising a silicon-based or equivalent substrate (See for example, Voldman et al., Ann. Rev. Biomed. Eng. 1:401-425, 1999). The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of MEMS may be fabricated using integrated circuit (IC) processes (for example, CMOS, Bipolar, or BICMOS processes). They may be patterned using photolithographic and etching methods known for computer chip manufacture. The micromechanical components may be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting. Methods for manufacture of nanoelectromechanical systems may be used for certain embodiments of the invention. (See, for example, Craighead, Science 290: 1532-36, 2000.)

In some embodiments of the invention, uniform nanoparticle substrates may be connected to various fluid filled compartments, such as microfluidic channels, nanochannels and/or microchannels. These and other components of the apparatus may be formed as a single unit, for example in the form of a chip, as known in semiconductor chips and/or microcapillary or microfluidic chips. Alternatively, the uniform nanoparticle substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz, and those having a gold surface layer, and the like.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. (See, for example, Craighead, *Science* 290:1532-36, 2000.) Various forms of microfabricated chips are commercially available from, for example, Caliper Technologies Inc. (Mountain View, Calif.) and ACLARA BioSciences Inc. (Mountain View, Calif.).

In certain embodiments of the invention, part or all of the apparatus may be selected to be transparent to electromagnetic radiation at the excitation and emission frequencies used for Raman spectroscopy, such as glass, silicon, quartz or any other optically clear material. For fluid-filled compartments that may be exposed to various analytes, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (for example, U.S. Pat. No. 6,263,286). Such modifications may include, but are not limited to, coating with commercially available capillary coatings (Supelco, Bellafonte, Pa.), silanes with various functional groups, such as polyethyleneoxide or acrylamide, or any other coating known in the art.

In certain aspects of the invention, a system for detecting the nanoparticles of the present invention includes an information processing system. An exemplary information processing system may incorporate a computer that includes a bus for communicating information and a processor for processing information. In one embodiment of the invention, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, or a Pentium Xeon® processor (Intel Corp., Santa Clara, Calif.). In various other embodiments of the invention, the processor may be based on Intel.® architecture, such as Intel® IA-32 or Intel® IA-64 architecture. Alternatively, other processors may be used. The information processing and control system may further comprise any peripheral devices known in the art, such as memory, display, keyboard and/or other devices.

In particular examples, the detection unit may be operably coupled to the information processing system. Data from the detection unit may be processed by the processor and data stored in memory. Data on emission profiles for various Raman labels may also be stored in memory. The processor may compare the emission spectra from composite organic-inorganic nanoparticles in the flow path and/or flow-through cell to identify the Raman-active organic compound. The processor may analyze the data from the detection unit to determine, for example, the sequence of a polynucleotide bound by a probe of the nanoparticles of the present invention. The information processing system may also perform standard procedures such as subtraction of background signals.

While certain methods of the present invention may be performed under the control of a programmed processor, in alternative embodiments of the invention, the methods may be fully or partially implemented by any programmable or hardcoded logic, such as Field Programmable Gate Arrays (FPGAs), TTL logic, or Application Specific Integrated Circuits (ASICs). Additionally, the disclosed methods may be performed by any combination of programmed general-purpose computer components and/or custom hardware components.

Following the data gathering operation, the data will typically be reported to a data analysis operation. To facilitate the analysis operation, the data obtained by the detection unit will typically be analyzed using a digital computer such as that described above. Typically, the computer will be appropriately programmed for receipt and storage of the data from the detection unit as well as for analysis and reporting of the data gathered. In certain aspects, custom designed software packages may be used to analyze the data obtained from the detection unit. In alternative embodiments of the invention, data analysis may be performed, using an information processing system and publicly available software packages.

Figure 9:
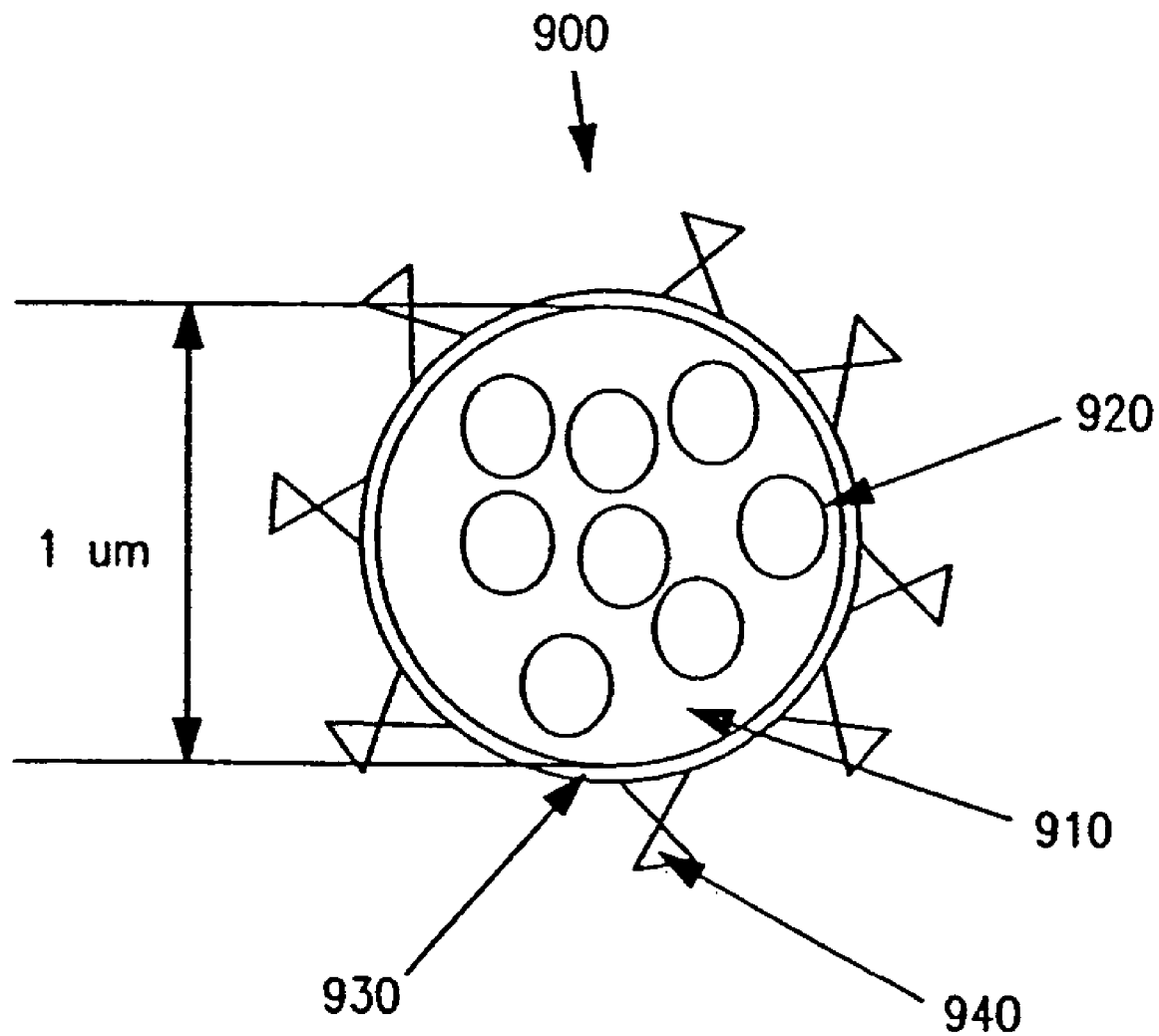
FIG. 9 illustrates a schematic of exemplary microspheres used in the invention methods as described herein.
Figure 10:
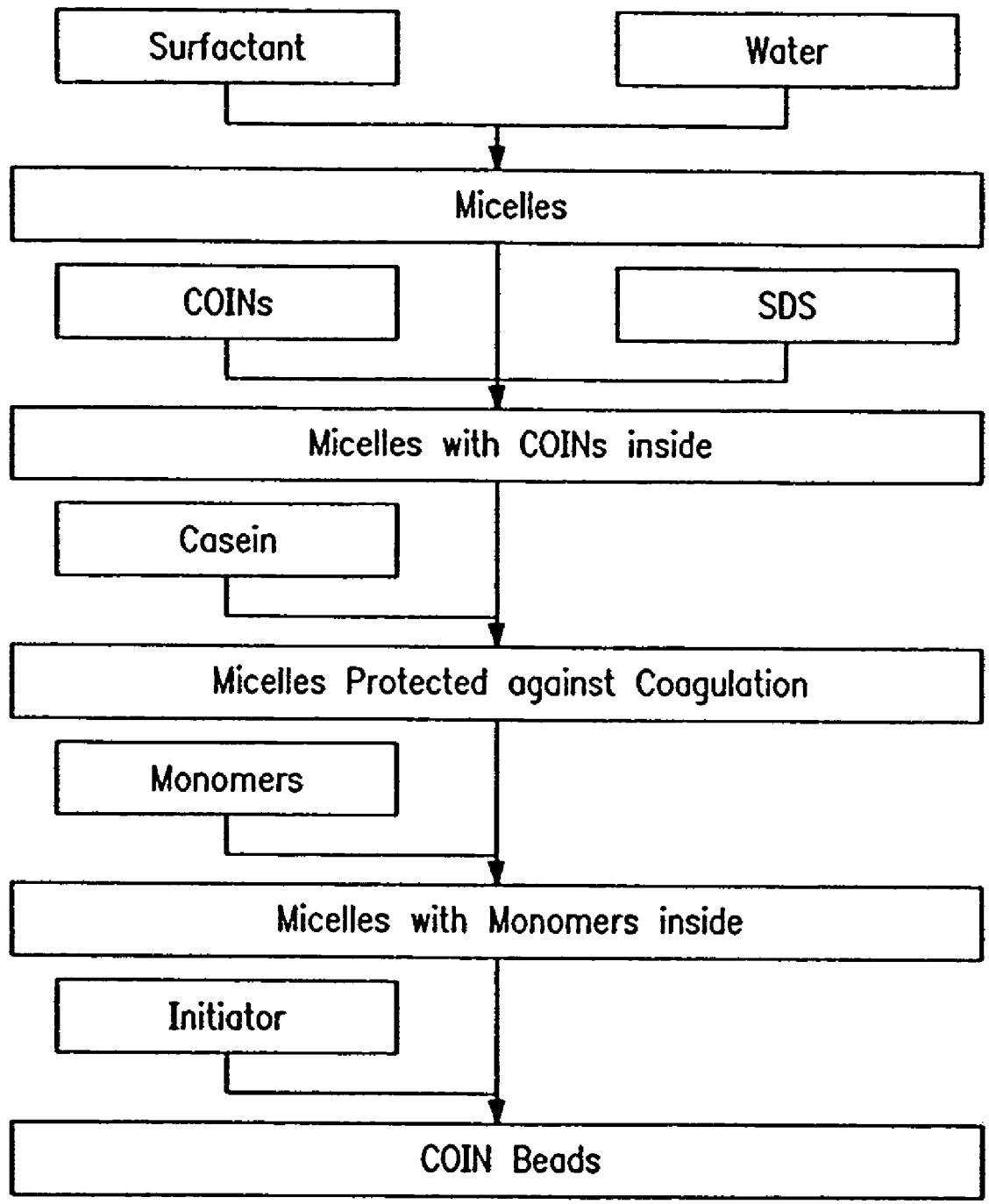
FIG. 10 is a flow chart illustrating one method (inclusion method) for producing the microspheres used in the invention methods.

Referring now to FIG. 9, microspheres 900 used in invention methods are about 1 μm in diameter and comprise two or more invention COINs or clusters of nanoparticles embedded and held together within a polymeric microsphere are used to make COIN-labeled probes will be discussed. The structural features are a) a structural framework 910 formed by polymerized organic compounds; b) multiple COINs 920 embedded in a micro-sized particle; c) a surface 930 with suitable functional groups for attachment of desired molecules 940, such as linkers, probes, and the like. Such microspheres produce stronger and more consistent SERS signals than individual COINs or nanoparticle clusters or aggregates. The polymer coating of the large microsphere may also provide sufficient surface areas for attachment of biomolecules, such as probes. Several methods for producing microspheres according to this embodiment are set forth below.

Inclusion method This approach employs the well-established emulsion polymerization technique for preparing uniform latex microspheres except that COINs are introduced into the micelles before polymerization is initiated. As shown in the flow chart of FIG. 10, this aspect of the invention methods involves the following steps: 1) micelles of desired dimensions are first prepared by homogenization of water with surfactants (for example octanol). 2) COIN particles are introduced along with a hydrophobic agent (for example SDS). The latter facilitates the transport of COINs into the interior of micelles. 3) Micelles are protected against aggregation with a stabilizing agent (for example Casein). 4) Monomers (for example styrene or methyl methacrylate) are introduced. 5) A free radical initiator (for example peroxide or persulfate) is used to start the polymerization to produce COIN embedded latex microspheres.

A refinement of the above approach uses clusters of nanoparticles or COIN particles that have been embedded within a solid organic polymer bead to form a microsphere. The polymer may prevent direct contact between nanoparticle clusters or COIN particles in the micelles and in the final product (microsphere). Furthermore, the number of nanoparticle clusters or COINs in a microsphere may be adjusted by varying the polymer thickness in the interstices of the microsphere. The polymer material of the microsphere is not needed for signal generation, the function of the polymer being structural.

The microspheres are about 1 to about 5 micrometers in average diameter and may operate as a functional unit having a structure comprising many individual COIN particles held together by the structural polymer of the microsphere. Thus, within a single microsphere are several COINs embedded in the structural polymer, which is the main inner and outer structural material of the bead. The structural polymer also functions as a surface for attaching linkers, derivatives, or for functionalization for attachment of probes. Since a COIN comprises a cluster of primary metal particles with at least one Raman-active organic compound adsorbed on the metal particles, the polymer of the bead for the most part does not come into contact with and hence does not attenuate Raman-activity of the Raman-active organic compounds which are trapped as they were adsorbed during colloid formation in the junctions of the primary metal particles or embedded in the metal atoms of the COIN structure. Those Raman-active organic molecules on the periphery of the COIN that may come into contact with the structural polymer of the microsphere have reduced effect as Raman-active molecules.

Figure 11:
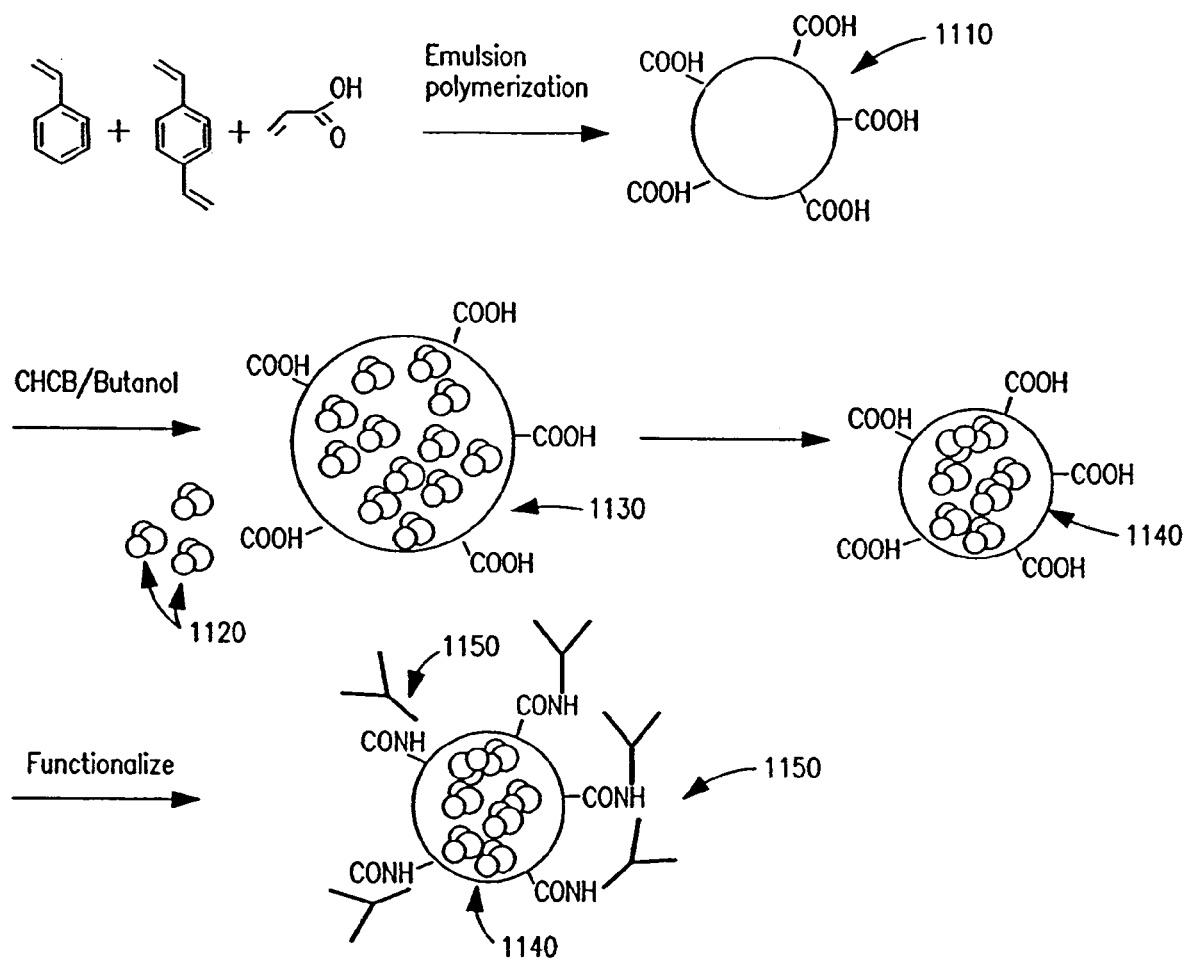
FIG. 11 is a flow chart illustrating one method (soak-in method) for producing the microspheres used in the invention methods.

Soak-in method Another method for making an the microspheres used in the invention methods is described with reference the flow chart in FIG. 11. Polymer beads 1110 are formed by emulsion polymerization. The polymer beads 1110 are subjected to an organic solvent, such as CHCB/butanol, which causes the beads to swell such that pores of the polymer bead become enlarged. COINs 1120 are contacted with the swollen polymer beads, allowing the COINs to diffuse inside. Changing the liquid phase to an aqueous phase causes the pores of the bead close, embedding the COINs within the polymer beads. For example, 1) styrene monomers are co-polymerized with divinylstyrene and acrylic acid to form uniformly sized beads through emulsion polymerization; 2) the beads are swelled with organic solvents such as chloroform/butanol, and a set of COINs at a certain ratio are introduced so that the COINs diffuse into the swollen bead; 3) the swollen beads are placed in a non-solvent to shrink the beads so that the COINs are trapped inside to form stable, uniform COIN-encapsulated microspheres 1140. The microspheres are functionalized with probes 1150, such as antibodies, to yield probe labeled microspheres 1150, which can be used in the place of probe-labeled COINs in the invention methods.

Figure 12:
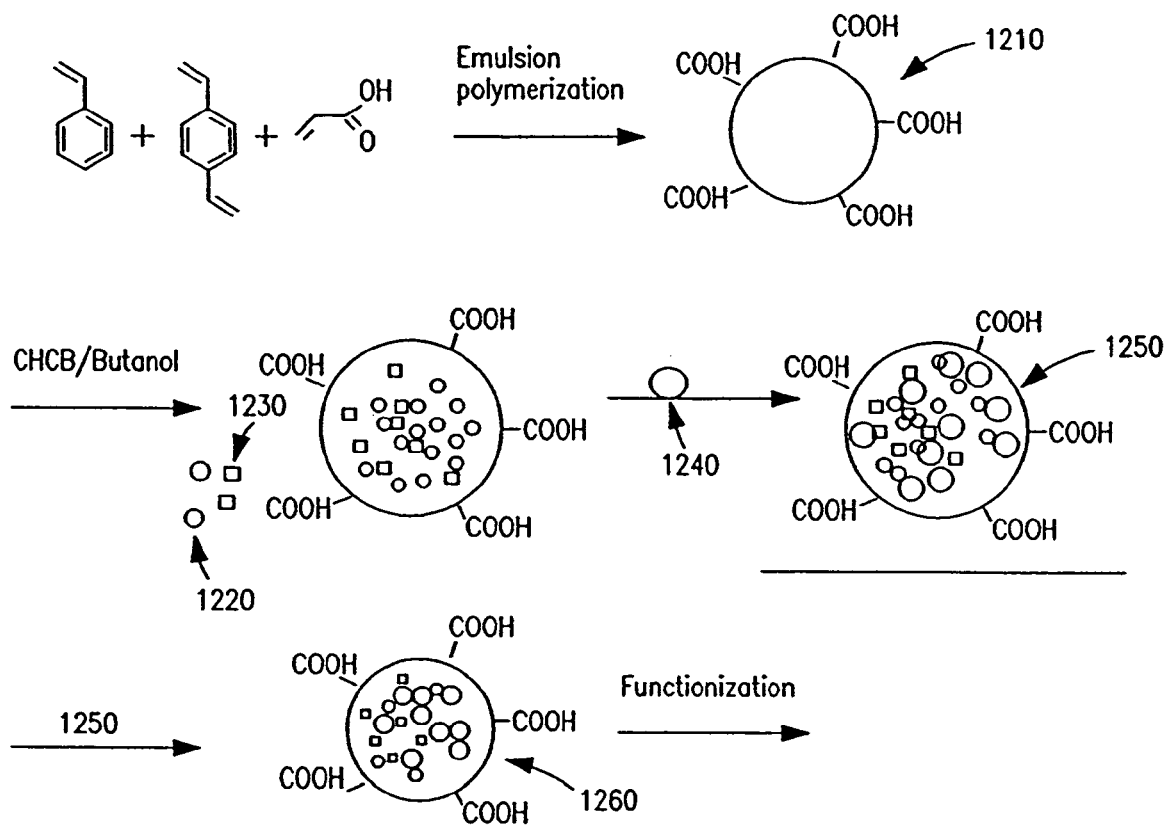
FIG. 12 is a flow chart illustrating one method (build-in method) for producing the microspheres used in the invention methods.

Build-in method Yet another method for making an the microspheres used in the invention methods is exemplified with reference to the flow diagram of FIG. 12. In this method, microsphere beads 1210 are obtained first and are placed in contact with Raman active organic molecules 1220, 1230 and silver colloids 1240 in organic solvents. Under this condition, the pores of the beads are enlarged enough to allow the Raman active molecule and silver colloids to diffuse inside the swollen polymer beads; the COIN clusters are formed inside the microspheres when silver colloids encounter one another in the presence of organic Raman labels 1250. Heat and light may be used to accelerate aggregation and fusion of silver particles. Finally, the liquid phase is changed to aqueous phase 1250, to yield COIN labeled microspheres 1260, which may be functionalized for attachment of probe molecules as described with reference to FIG. 11 above. For example, 1) styrene monomers are co-polymerized with divinylstyrene and acrylic acid to form uniformly sized beads through emulsion polymerization; 2) the beads are swelled with organic solvents such as chloroform/butanol, and a set of Raman-active molecules (for example, 8-aza-adenine and N-benzoyladenine) at a certain ratio is introduced so that the molecules diffuse into the swollen bead—Ag colloid suspension in the same solvent is then mixed with the beads to form Ag particle-encapsulated beads; 3) the solvent is switched to one that shrinks the beads so that the Raman labels and Ag particles are trapped inside. The process may be controlled so that the Ag particles will contact one another with Raman molecules in the junction, forming COIN inside the beads. When medium size silver colloids such as 60 nm are used, Raman labels are added separately (before or after silver addition) to induce colloid aggregation (formation of COINs) inside the beads. When 1-10 nm colloids are used, the labels may be added together. Then light or heat is used to induce the formation of active COINs inside the microspheres.

Figure 13:
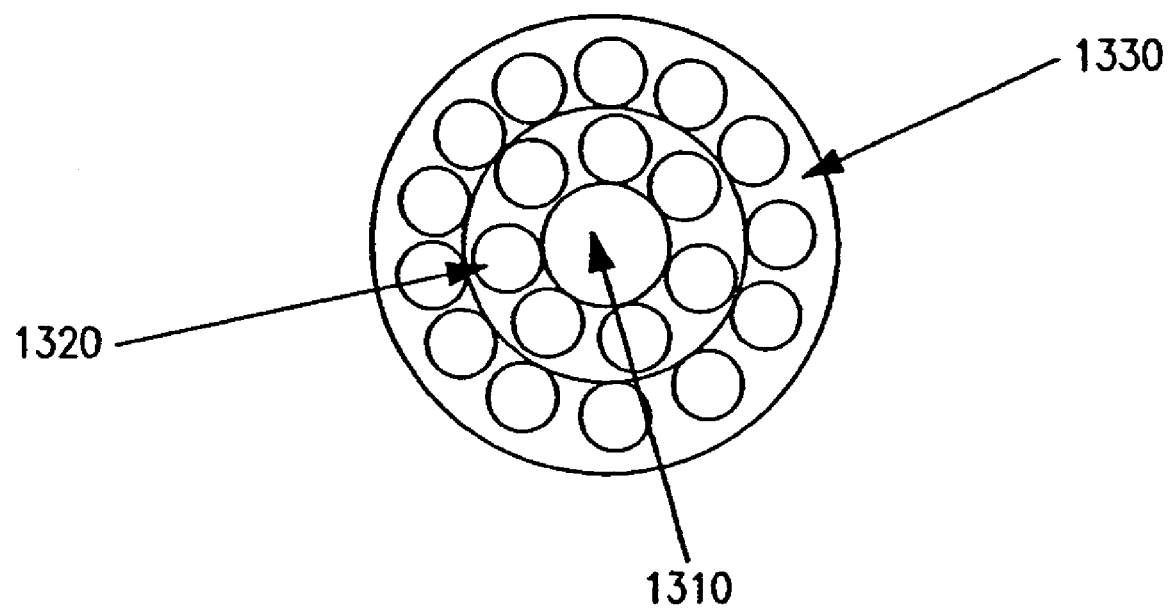
FIG. 13 is a flow chart illustrating one method (build-out method) for producing the microspheres used in the invention methods.

Build-out method Another method for making the microspheres used in the invention methods is described with reference to FIG. 13. In this method, a solid core 1310 is used first as the support for COIN attachment. The core may be metal (gold and silver), inorganic (alumina, hematite and silica) or organic (polystyrene, latex) particles. Electrostatic attraction, van der Waals forces, and/or covalent binding induce attachment of COINs 1320 to the core particle. After the attachment, the assembly may be coated and filled in with a polymer material 1330 to stabilize the structure and at the same time to provide a surface with functional groups. Multiple layers of COINs may be built based on the above procedure. The dimension of COIN beads may be controlled by the size of the core and the number of COIN layers. For example, 1) positively charged Latex particles of 0.5 μm are mixed with negatively charged COINs; 2) the Latex-COIN complex is coated with a cross-linkable polymer such as poly-acrylic acid; 3) the polymer coating is cross-linked with linker molecules such as lysine to form an insoluble shell. Remaining (unreacted) carboxylic groups would serve as the functional groups for second layer COIN attachment or probe attachment. Additional functional groups may also be introduced through co-polymerization or during the cross-link process.

For multiplex tests in a complex sample, a coding system that possesses identifiers for a large number of reactants in the sample may be included. A variable that determines the achievable numbers of identifiers in currently known coding systems is the physical dimension. Tagging techniques based on surface-enhanced Raman scattering (SERS) of fluorescent dyes indicate that chemical structure-based coding systems may be developed. The organic compound-assisted metal fusion (OCAM) method used to produce composite organic-inorganic nanoparticles (COIN) that are highly effective in generating SERS signals allows synthesis of COIN from a wide range of organic compounds to produce sufficient distinguishable COIN Raman signatures to assay any complex biological sample. Thus COIN may be used as a coding system for multiplex and amplification-free detection of bioanalytes at near single molecule levels.

COINs generate intrinsic SERS signal without additional reagents. Using the OCAMF-based COIN synthesis chemistry, a large number of different COIN signatures may be generated by mixing a limited number of Raman labels for use in multiplex assays. In one scenario, the Raman spectrum of a sample labeled with COIN may be characterized by three parameters:

(a) peak position (designated as L), which depends on the chemical structure of Raman labels used and the umber of available labels, (b) peak number (designated as M), which depends on the number of labels used together in a single COIN, and (c) peak height (designated as i), which depends on the ranges of relative peak intensity.

The total number of possible Raman signatures (designated as T) may be calculated from the following equation:

$$T = \sum_{k=1}^{M} \frac{L!}{(L-k)!k!} P(i, k)$$

where $P(i, k)=i^k-i+1$, being the intensity multiplier which represents the number of distinct Raman spectra that may be generated by combining k (k=1 to M) labels for a given i value. The multiple labels may be mixed in various combination numbers and ratios to make the multiple COINs. Spectral signatures having closely positioned peaks (15 cm$^{-1}$) may be resolved visually. Theoretically, over a million of COIN signatures may be made within the Raman shift range of 500-2000 cm$^{-1}$ by incorporating multiple organic molecules into COIN as Raman labels using the OCAMF-based COIN synthesis chemistry. Thus, OCAMF chemistry allows incorporation of a wide range of Raman labels into metal colloids to perform parallel synthesis of a large number of COINs with different Raman signatures in a matter of hours by mixing several organic Raman-active compounds of different structures, mixtures, and ratios for use in the invention methods described herein.

In various embodiments, the analyte to be detected may comprise a cellular protein, which may be a protein that is expressed in the cell (either a normal or a mutant protein) or an exogenous protein that otherwise is present in the cell due, for example, to uptake by the cell, to infection of the cell by an organism (for example, a bacterium or virus), or to introduction of the protein (or an encoding polynucleotide) using biological, biochemical methods, or molecular biological techniques (for example, introducing a vector containing a polynucleotide into a cell, wherein the analyte comprises the polynucleotide or a polypeptide encoded by the polynucleotide). As such, the present methods may identify a target molecule in a cell, which may be a living cell.

In one aspect, invention methods are provided for using COIN for cell imaging, including, for example, for an in situ hybridization assay or for an antibody (or receptor) based assay. In situ hybridization allows the localization and detection of specific nucleic acid sequences in cell preparations, preserved tissue sections, and the like. Such a method may be performed using a COIN-labeled oligonucleotide that is complementary to the target nucleic acid sequence. Similarly, an antibody based assay may utilize COIN-labeled antibodies specific for a target protein, and a receptor based assay may utilize a COIN-labeled receptor (or ligand) that specifically binds a ligand (or receptor) of a cell. Also, a COIN-labeled protein may be utilized to identify one or more proteins that specifically interact with the COIN-labeled protein (for example, proteins in an intracellular pathway, or proteins that are expressed by an infecting organism that may interact with and effect the activity of an intracellular protein. The use of COIN as a Raman label provides advantages as disclosed herein, including, for example, multiple different unique COIN signatures may be utilized in a single assay, thus permitting multiplex signals to be detected in a single sample.

The cell based screening methods may be performed using COIN-labeled probe(s) prepared as disclosed herein and using the variously disclosed formats. For example, the COIN-probes may be contacted with a cell sample, under conditions and for a sufficient time for the COIN-probe to interact with the target molecule. Then SERS spectra of the COIN-probes(s) may be collected across the cell sample and a SERS image based on the COIN signal(s) at specific locations of the cell may be reconstructed. For example, genotyping information may be obtained based on the binding locations and types of COIN-probes detected, and the genotype information may be correlated with disease states (or the potential for a disease state).

Genotyping information that may be obtained according to the invention methods may include, for example, the identification of a particular mutation or a single nucleotide polymorphism (or haplotype) known to be associated with a particular disease state (or predisposition to the disease state) or other condition (for example, sensitivity to a particular drug therapy of a subject from whom the cell was obtained). The mutations may be single nucleotide transitions or transversions, or deletions or insertions. The mutations also may be chromosomal translocations or duplications of chromosomal regions (for example, amplification of chromosomal regions), which may be diagnostic of a particular type of cancer or other disorder, or may be indicative of drug resistance or susceptibility (for example, susceptibility to a bacterium infecting the cell).

For cell imaging applications, the COINs are functionalized to specific probes such as DNA or RNA oligonucleotides (or such oligonucleotides containing one or more nucleotide analogs and/or bonds other than phosphodiester bonds; for example, a peptide or phosphothioester bond), antibodies (for example, monoclonal antibodies, or antigen binding fragments of an antibody (for example, an Fab fragment), receptors (or ligands for particular receptors). Referring to FIG. 14, functionalization of COIN(s) to probe(s) may be facilitated using a microfluidic array assembly. Microfluidic array assembly 1400 includes a buffer (wash solution) reservoir 1 from which fluid is introduced into a fluid channel, which may contain one or more valves that may be opened or closed to allow or prevent, respectively, passage of fluid, and may contain a porous membrane. At least one COIN reservoir 1410, which in this illustrative example contains nine different COINs (illustrated by COINs A, B, C, etc.), each of which may be selected for functionalization to an individual probe of known binding specificity contained in at least one probe reservoir 1430 (illustrated by probes X1, X2, X3, etc). As used herein, the term "at least one" means one, two, three, four, or more (e.g., 5, 6, 7, 8, 9, 10, 15, 20, or more). As such, a microfluidic array assembly can have, for example, 1, 2, 3, or more COIN reservoirs 1410 (e.g., a set of 2, 3, 4, or more COIN reservoirs 1410) and/or 1, 2, 3, or more probe reservoirs 1430 (e.g., a set of 2, 3, 4, or more probe reservoirs 1430). COIN-probe conjugates are formed by pumps (triangles) effecting flow of fluid into mixing reservoir 2. Where a microfluidic array assembly has, for example, 2, 3, 4 or more COIN reservoirs 1410 and/or 2, 3, 4 or more probe reservoirs 1430, at least one type of COIN and at least one type of probe may be selected, wherein valves on the reservoirs containing the selected COIN(s) and/or probe(s) are opened to allow flow into the fluid channel and into mixing reservoir 2. Within the mixing reservoir 2, COIN solution and probe solution may mix by any means, including, for example, diffusion mixing, mechanical mixing, electrical mixing, magnetic mixing, and/or fluidic mixing. The content of mixing reservoir 2 may be flowed into separation chamber 3 for separation of functionalized COIN-probe conjugates from unconjugated COIN and/or probe. A porous membrane located within the fluid channel may be used as a separator, for example. COIN-probe conjugates may be flowed and held in COIN-probe chamber 4. Array 1460 exemplifies COIN-probe conjugates (illustrated by AX1, BX2, CX3, etc.), wherein each COIN-probe conjugate comprises a unique COIN, that may be flowed into and held in COIN-probe chamber 4. Unconjugated COIN and/or probe may be flowed into waste reservoir 5. A blocking agent held in reservoir 6 may be introduced via a fluid channel into mixing/separation chamber 7 to block any additional active sites on the COIN in the COIN-probe conjugate. An additional waste reservoir may be included to hold waste fluids collected downstream. Using such a microfluidic assay assembly, a plurality of different combinations of COIN-probe conjugates may be prepared, 81 different combinations in the example shown in FIG. 14. Additional wash water reservoirs may be added to the microfluidic assembly to incorporate wash steps, as desired, in the fabrication of COIN-probes. The microfluidic array assembly may be located on a chip as described herein.

The cell sample to be detected with the COIN-probes may be immobilized on a solid substrate (for example, gold/silicon, or glass), such as a chip containing one or more arrays. The cells of the sample may, but need not, be grown in culture medium on the substrate, and immobilized using a solvent (for example., 100% acetone). Where a COIN-probe is used to identify a target molecule within a cell, use of a solvent, such as acetone, provides the advantage of making the cell porous. Cell porosity may facilitate entry of a COIN-probe into the cells. Alternatively, other agents, such as a detergent, may be used to facilitate entry of a COIN-probe into a cell. FIG. 15A shows the optical image of cells immobilized on a solid substrate (FIG. 15B illustrates a control substrate in which no cells were present in the culture medium).

The COIN-probes then are contacted with the cell sample (for example, the immobilized cell sample). When the probes contact a target molecule (for example, DNA, mRNA, or a protein) expressed on the surface of the cell or present in the cell, specific binding occurs, anchoring the COIN-probe to the target molecule. Scanning of a laser light across the sample causes the COIN to generate a SERS signal. The laser light can be held fixed, and the sample, which may be on a nano-positioning stage may move in the x-axis and y-axis in defined steps (for example, 1 μm steps). An additional benefit of SERS cell imaging of COIN-probes is the ability to detect signal using only one excitation wavelength, which may be selected to be in the near infrared range (for example, about 800 nm) to minimize potential inherent fluorescence of the cell sample, or may be selected to be in a non-infrared range (e.g., about 514 to 532 nm).

Figure 16:
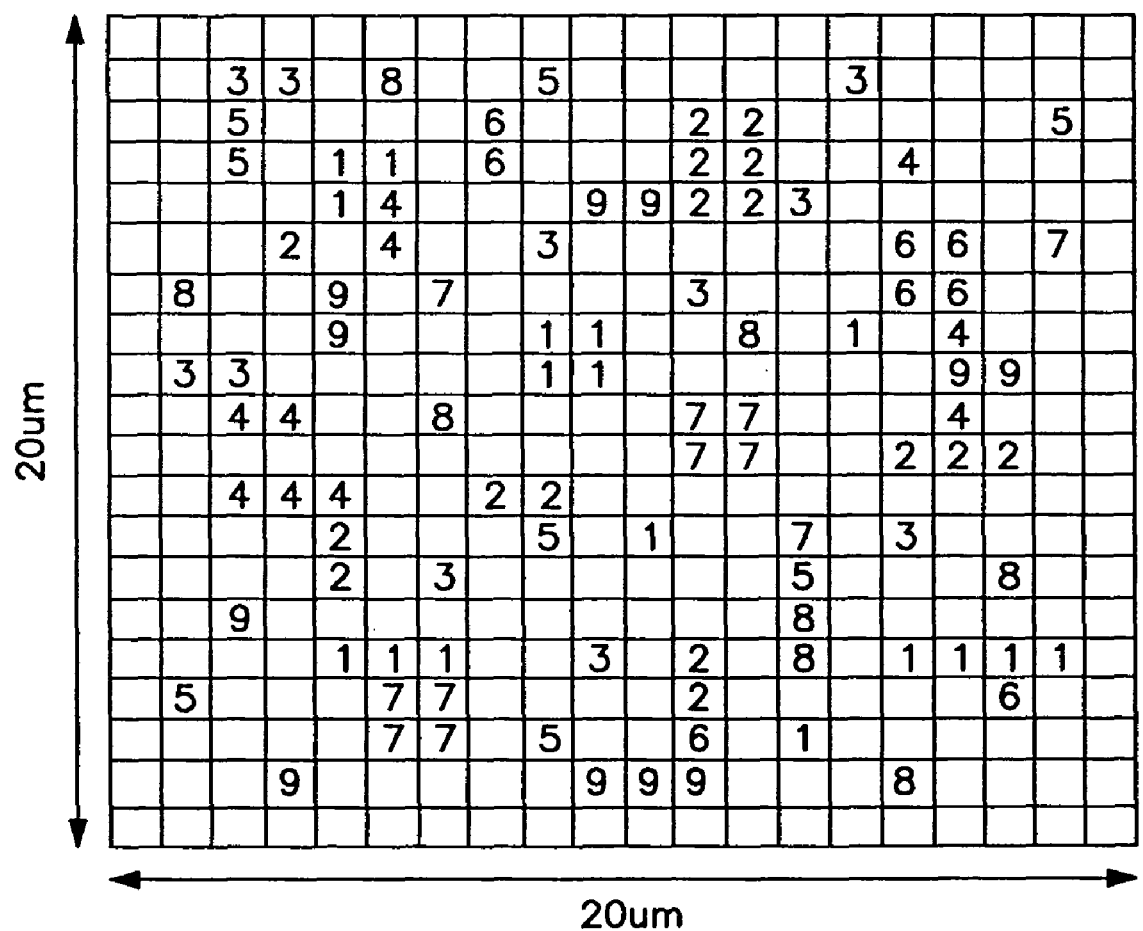
FIG. 16 illustrates multiplex COIN signals emanating from COIN-probes bound at a multiplicity of locations within in a cell sample.

FIG. 16 provides a representative picture of a cell image, wherein each number represents a unique COIN signal coming for a COIN-probe conjugate bound at a defined location within the cell immobilized on the substrate. The location of the COIN signal identifies the position of the target molecule within the cell. For example, such a COIN signal may identify a translocation of a chromosome where the probe of a COIN-probe comprises a nucleic acid molecule that binds specifically to a known gene sequence indicative of the translocated portion of the chromosome. FIG. 16 demonstrates the multiplex advantage provided by using COINs as SERS labels for a specific probe. As such, COIN-probes provide an advantage over other Raman labels used to examine cells, including, for example, colloidal gold particles (see, for example, Kneipp et al., *Appl. Spectroscopy* 56:150, 2002).

The invention is further described by the following non-limiting example.

EXAMPLE 1

Antibody-COIN conjugation: To conjugate COIN particles with antibodies, a direct adsorption method was used. A 500 μL solution containing 2 ng of a biotinylated anti-human IL-2 (anti-IL-2), or IL-8 antibody (anti-IL-8), in 1 mM Na₃Citrate (pH 9) was mixed with 500 μL of a COIN solution (using 8-aza-adenine or N-benzoyl-adenine as the Raman label). The resulting solution was incubated at room temperature for 1 hour, followed by adding 100 μL of PEG-400 (polyethylene glycol 400). The solution was incubated at room temperature for another 30 min before a 200 μL of 1% TWEEN-20 detergent was added. The resulting solution was centrifuged at 2000×g for 10 min. After removing the supernatant, the pellet was resuspended in 1 mL solution (BSAT) containing 0.5% BSA, 0.1% TWEEN-20™ detergent and 1 mM Na₃Citrate. The solution was again centrifuged at 1000×g for 10 min to remove the supernatant. The BSAT washing procedure was repeated for a total of 3 times. The final pellet was resuspended in 700 μL of Diluting Solution (0.5% BSA, 1×PBS, 0.05% Tween-20). The Raman activity of a conjugated COIN sample was measured and adjusted to a specific activity of about 500 photon counts (from main peak) per μL per 10 seconds using a Raman microscope that generated about 600 counts from methanol at 1040 cm$^{-1}$ for 10 second collection time.

Immuno sandwich assays Xenobind™ aldehyde slides (Xenopore Inc., N.J., USA) were used as substrates for immuno sandwich assays; before being used, wells on a slide were prepared by overlaying a slab of cured poly(dimethyl siloxane) (PDMS) elastomer of 1 mm thickness. Holes approximately, 5 mm in diameter were punched into the PDMS slab. To immobilize capture antibodies, 50 μL of an antibody (9 μg/mL) in 0.33×PBS was added to wells and the slide was incubated in a humidity chamber at 37° C. for 2 hours. After removing free antibodies, 50 μL of 1% BSA in a 10 mM glycine solution was added to the wells to inactivate the aldehyde groups on the slide. The slide was incubated at 37° C. for another 1 hour before the wells were washed 4 times, each with 50 μL PBST washing solution (1×PBS, supplemented with 0.05% TWEEN-20™ detergent).

Antigen binding and detection antibody binding (antibody-COIN conjugate binding) were carried following instructions from the antibody supplier (BD Biosciences). After removing the unbound conjugates, the wells were washed 4 times, each with 50 μL of washing solution. Finally, 30 μL of washing solution was added to wells before competitive binding. To demonstrate competitive binding, interleukin-2 protein (IL-2, 10 ng/mL) may be added to wells with anti-IL-2 capture antibody; anti-IL-2 antibody-coated COIN particles are used to binding to the captured IL-2 molecules in the binding complexes. After washing the wells with buffer, samples containing different amounts of IL-2 were added separately to the wells. The solutions containing released COINs from wells were detected for COIN signals with a Raman scope.

REFERENCES

1. Fodor, S. P. et al. Multiplexed biochemical assays with biological chips. *Nature* 364, 555-556 (1993).

2. MacBeath, G. & Schreiber, S. L. Printing proteins as microarrays for high-throughput function determination. *Science* 289, 1760-1763 (2000).

3. Nicewarner-Pena, S. R. et al. Submicrometer metallic barcodes. *Science* 294, 137-141 (2001).

4. Alivisatos, A. P. Perspectives on the physical chemistry of semiconductor nanocrystals. *J. Phys. Chem.* 100, 13226-13239 (1996).

5. Isola, N. R., Stokes, D. L. & Vo-Dinh, T. Surface-Enhanced Raman Gene Probe for HIV Detection. *Anal. Chem.* 70, 1352-1356 (1998).

6. Ni, J., Lipert, R. J., Dawson, G. B. and Porter, M. D. Immunoassay Readout Method Using Extrinsic Raman Labels Adsorbed on Immunogold Colloids. *Anal. Chem.* 71, 4903-4908 (1999).

7. Graham, D., Mallinder, B. J., Whitcombe, D., Watson, N. D. & Smith, W. E. Simple multiplex genotyping by surface-enhanced resonance Raman scattering. *Anal. Chem.* 74, 1069-1074 (2002).

8. Cao, Y. W. C., Jin, R. & Mirkin, C. A. Nanoparticles with Raman spectroscopic fingerprints for DNA and RNA detection. *Science* 297, 1536-1540 (2002).

9. Doering, W. E. & Nie, S. Spectroscopic tags using dye-embedded nanoparticles and surface-enhanced Raman scattering. *Anal Chem.* 75, 6171-6176 (2003)

10. Mulvaney, S. P., Musick, M. D., Keating, C. D. & Natan, M. J. Glass-coated, analyte-tagged nanoparticles: a new tagging system based on detection with surface-enhanced Raman scattering, *Langmui.* 19, 4784-4790 (2003).

11. Grubisha, D., Lipert, R. J., Park, H. Y., Driskell, J. & Porter, M. D. Femtomolar Detection of Prostate Specific Antigen: an Immunoassay Based on Surface-Enhanced Raman Scattering and Immunogold Labels. *Anal. Chem.* 75, 5936-5943 (2003).

12. Kneipp, K., Wang, Y., Kneipp, H., Perelman, L. T., Itzkan, I., Dasari, R. & Feld, M. S. Single molecule detection using surface-enhanced Raman scattering (SERS). *Physical Review Letters* 78, 1667-1670 (1997).

13. Nie, S. & Emory, S. R. Probing single molecules and single nanoparticles by surface-enhanced Raman scattering, *Science* 275, 1102-1106 (1997).

14. Xu, H, Bjemeld, E. J., Käll, M., & Börjesson, L. Spectroscopy of single hemoglobin molecules by surface enhanced Raman scattering, *Phys. Rev. Lett.* 83, 4357-4360 (1999).

15. Xu, H., Aizupurua, J., Käll, M. & Apell, P. Electromagnetic contributions to single-molecule sensitivity in surface-enhanced Raman scattering. *Physical Review E.* 62, 4318-4324 (2000).

16. Michaels, A. M., Nirmal, M. & Brus, L. E. Surface Enhanced Raman Spectroscopy of Individual Rhodamine 6G Molecules on Large Ag Nanocrystals. *J. Am Chem Soc.* 121, 9932-9939. (1999).

17. Kerker, M. Electromagnetic Model for Surface-Enhanced Raman Scattering (SERS) on Metal Colloids. *Acc. Chem. Res.* 17, 271-277 (1984).

18. Campion, A. & Kambhampati, P. Surface-enhanced Raman scattering, *Chem. Soc. Rev.* 27, 241-250 (1998).

19. Kneipp, K., Kneipp, H., Itzkan, I., Dasari, R. R. & Feld, M. S. Ultrasensitive chemical analysis by Raman spectroscopy. *Chemical Reviews* 99, 2957-2975 (1999).

20. Kambhampati, P., Child, C. M., Foster, M. C. & Campion, A. On the chemical mechanism of surface enhanced Raman scattering: Experiment and theory. *J. Chem. Phys.* 108, 5013-5026 (1998).

21. Otto, A, Mrozek, I, Grabhom, H. & Akemann W. Surface Enhanced Raman Scattering, *Journal of Physics: Condensed Matter vol.* 4, 1143-1212(1992).

22. Emory, S. R., Haskins, W. E. & Nie, S. Direct observation of size-dependent optical enhancement in single metal nanoparticles. *J. Am. Chem. Soc.* 120, 8009-8010 (1998).

23. Michaels, A. M., Jiang, J. & Brus, L. Ag Nanocrystal Junctions as the Site for Surface-Enhanced Raman Scattering of Single Rhodamine 6G Molecules. *J. Phys Chem B* 104 11965-11971 (2000).

24. Bosnick, K. A., Jiang, J. & Brus, L. E. Fluctuations and local symmetry in single-molecule Rhodamine 6G Raman scattering on silver nanocrystal aggregates. *J. Phys. Chem. B.* 106, 8096-8099 (2002).

25. Jiang J., Bosnick, K., Maillard, M., & Brus, L., Single Molecule Raman Spectroscopy at the Junctions of Large Ag Nanocrystals. *J. Phys. Chem. B* 107, 9964-9972 (2003).

26. Duffy, D., McDonald, J., Schueller, O. & Whitesides, G. Rapid Prototyping of Microfluidic Systems in Poly(dimethylsiloxane). *Anal. Chem.* 70, 4974-4984 (1998).

Although the invention has been described with reference to the above example, it will be understood that modifications and variations are encompassed within the spirit and scope of the invention. Accordingly, the invention is limited only by the following claims.

What is claimed is:

1. A method for identifying a cell, a group of cells, or a component of a cell, in a sample, comprising:
contacting one or more samples immobilized on a solid substrate with at least two types of composite organic-inorganic nanoparticle (COIN) labeled probes such that the at least two types of the COIN labeled probes are different and emit a distinguishable surface enhanced Raman spectroscopy (SERS) signature, under conditions suitable to at least allow specific binding of the probes to a known cell component of the sample to form Raman-active complexes, wherein a first type of the COIN labeled probe includes a different metal than that in a second type of the COIN labeled probe of said at least two types of the COIN labeled probes;
forming a COIN-containing complex comprising said one or more samples and said at least two types of COIN labeled probes;
illuminating the sample with a light source;
detecting SERS signatures of the least two types of COIN labeled probes, wherein a SERS signature is indicative of the presence of a cell or a component of a cell in the sample, wherein the SERS spectra of the COIN labeled probes are collected across the sample and SERS images based on the COIN signals at specific locations of the cell sample are constructed for identification of a cell, a group of cells or a component of a cell in the sample.

2. The method of claim 1, which comprises contacting a plurality of samples with at least one COIN-labeled probe.

3. The method of claim 1, which comprises contacting the sample with a plurality of COIN-labeled probes, wherein different probes of the plurality specifically bind to different cell components.

4. The method of claim 3, comprising detecting, in a multiplex fashion distinguishable SERS signatures emitted by COIN-labeled probes of the plurality.

5. The method of claim 3, comprising contacting a plurality of samples with the plurality of COIN-labeled probes.

6. The method of claim 1, wherein the sample comprises a sample obtained from a human subject.

7. The method of claim 6, wherein the sample comprises a cell, tissue, or organ sample.

8. The method of claim 7, wherein the sample is obtained from a subject having or suspected of having a known disorder.

9. The method of claim 8, wherein the disorder comprises a genetic mutation or an infection with a microorganism.

10. The method of claim 9, wherein microorganism is a bacterium, a virus, a fungus, or a yeast.

11. The method of claim 5, wherein the components of the cells of the samples comprise proteins, and wherein the SERS signatures provide a protein profile of the cells.

12. The method of claim 5, wherein the components of the cells of the samples comprise nucleic acid molecules, and wherein the SERS signatures provide a genetic profile of the cells.

13. The method of claim 5, wherein cells from different samples obtained from a subject are located on different arrays.

14. The method of claim 13, wherein two to four different arrays are used.

15. The method of claim 1, wherein the probe comprises a polypeptide, a polynucleotide, or a combination thereof.

16. The method of claim 15, wherein the polypeptide is an antibody, or an antigen binding fragment of an antibody.

17. The method of claim 1, wherein the sample is immobilized on the substrate.

18. A method for identifying a structure in a sample cell comprising:
  contacting one or more cells immobilized on a solid substrate with at least two types of COIN-labeled probes such that each of the at least two types of the COIN labeled probes is different and emit a known distinguishable SERS signal, under conditions suitable for at least specific binding of a probe to a known target structure of a cell, wherein a first type of the COIN labeled probe includes a different metal than that in a second type of the COIN labeled probe in said at least two types of COIN labeled probes;
  forming a COIN-containing complex comprising said one or more samples and said at least two types of COIN labeled probes;
  illuminating the one or more cells with a light source; and
  detecting SERS signals from the at least two types of COIN-labeled probes in the sample cell, wherein a known SERS signal indicates presence of the target structure in the cell sample wherein the position of the target structure within the cell sample is located by the cell image based on the SERS signal produced by at least two types of COIN labeled probes.

19. The method of claim 18, which comprises contacting a plurality of sample cells with the one or more COIN-labeled probes, wherein cells of the plurality are in an array on the substrate.

20. The method of claim 19, which comprises contacting cells of the plurality of sample cells with a plurality of the COIN-labeled probes.

21. The method of claim 20, comprising detecting multiplex SERS signals from at least one sample cell of the plurality of cells.

22. The method of claim 21, further comprising collecting the SERS signals to provide a profile of the target structures in the sample cell.

23. The method of claim 22, further comprising comparing the profile with a cell profile similarly obtained from a reference cell of the same type.

24. The method of claim 23, wherein a difference in the profile of the sample cell as compared with the profile of the reference cell is indicative of an anomaly of the sample cell.

25. The method of claim 1, wherein the second metal is Ag, Au, Pt, Cu, Zn, or Fe.

26. The method of claim 1, wherein the second metal provides aqueous stability.

27. The method of claim 1, wherein the detecting one or more SERS signatures is without signal amplification.

28. The method of claim 1, wherein the sample comprises a mixture of the group of cells or components of the cell that are spotted onto individual defined locations by a reverse phase assay of the sample.

29. The method of claim 1, wherein at least the first type of COIN labeled probe comprises at least two different metals.

30. The method of claim 18, wherein the detecting one or more SERS signals is without signal amplification.

31. The method of claim 18, wherein the sample cell comprises a mixture of cells or components of the cell that are spotted onto individual defined locations by a reverse phase assay of the sample.

32. The method of claim 18, wherein at least the first type of COIN labeled probe comprises at least two different metals.

33. The method of claim 18, wherein the target structure in the cell is identified from the image.

* * * * *